United States Patent
Kohane et al.

(10) Patent No.: US 11,071,714 B2
(45) Date of Patent: Jul. 27, 2021

(54) POLY(KETALS) AND RELATED COMPOSITIONS AND METHODS

(71) Applicant: Children's Medical Center Corporation, Boston, MA (US)

(72) Inventors: Daniel S. Kohane, Newton, MA (US); Shutao Guo, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/096,794

(22) PCT Filed: Apr. 28, 2017

(86) PCT No.: PCT/US2017/030041
§ 371 (c)(1),
(2) Date: Oct. 26, 2018

(87) PCT Pub. No.: WO2017/189953
PCT Pub. Date: Nov. 2, 2017

(65) Prior Publication Data
US 2019/0365652 A1  Dec. 5, 2019

Related U.S. Application Data

(60) Provisional application No. 62/329,443, filed on Apr. 29, 2016.

(51) Int. Cl.
| | |
|---|---|
| A61K 9/16 | (2006.01) |
| A61K 9/00 | (2006.01) |
| A61K 9/19 | (2006.01) |
| A61K 31/095 | (2006.01) |
| A61K 31/198 | (2006.01) |
| A61K 31/401 | (2006.01) |
| A61K 31/5575 | (2006.01) |
| A61K 31/568 | (2006.01) |
| A61K 31/573 | (2006.01) |
| A61K 31/575 | (2006.01) |
| A61K 45/06 | (2006.01) |

(52) U.S. Cl.
CPC .......... *A61K 9/1641* (2013.01); *A61K 9/0048* (2013.01); *A61K 9/0053* (2013.01); *A61K 9/19* (2013.01); *A61K 31/095* (2013.01); *A61K 31/198* (2013.01); *A61K 31/401* (2013.01); *A61K 31/5575* (2013.01); *A61K 31/568* (2013.01); *A61K 31/573* (2013.01); *A61K 31/575* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,713,441 A | 12/1987 | Heller et al. | |
| 4,765,973 A | 8/1988 | Heller | |
| 5,374,681 A | 12/1994 | Kroner et al. | |
| 7,220,414 B2 | 5/2007 | Brocchini et al. | |
| 7,838,619 B2 | 11/2010 | Papisov | |
| 7,951,898 B2 | 5/2011 | Papisov | |
| 8,252,846 B2 | 8/2012 | Murthy et al. | |
| 2010/0150832 A1* | 6/2010 | Papisov ................. | C08L 59/02 424/1.65 |
| 2013/0281637 A1 | 10/2013 | Ueno et al. | |
| 2014/0072513 A1 | 3/2014 | Pena Gulin | |
| 2014/0315786 A1* | 10/2014 | Jirousek ................ | A61K 31/60 514/1.5 |
| 2014/0378426 A1* | 12/2014 | Hanneken ........... | A61K 31/565 514/182 |

(Continued)

FOREIGN PATENT DOCUMENTS

| | | | | |
|---|---|---|---|---|
| EP | 2508544 A1 * | 10/2012 | .......... | C08F 299/022 |
| WO | WO-2008127532 A1 * | 10/2008 | ........ | A61K 47/6907 |
| WO | WO 2016/059391 A1 | 4/2016 | | |

OTHER PUBLICATIONS

Maity et al ("A biodegradable adamantane polymer with ketal linkages in its backbone for gene therapy", Chem. Commun., 2015, vol. 51, p. 15956-15959).*

Gimenez et al ("Demonstrating the importance of polymer-conjugate conformation in solution on its therapeutic out: Diethylstilbestrol (DES)-polyacetals a prostate cancer treatment", Journal of Controlled Release, vol. 159 (2012), p. 290-301) (Year: 2012).*

International Search Report and Written Opinion dated Aug. 14, 2017 in connection with International Application No. PCT/US17/030041.

International Preliminary Report on Patentability dated Nov. 8, 2018 in connection with International Application No. PCT/US17/030041.

(Continued)

*Primary Examiner* — Sin J Lee

(74) *Attorney, Agent, or Firm* — Wolf, Greenfield & Sacks, P.C.

(57) ABSTRACT

Compositions comprising polymers comprising one or more ketal, monothioketal, and/or thioketal bonds are provided, as well as related methods and kits. In some embodiments, a polymer may comprise one or more repeat units comprising one or more ketal, monothioketal, and/or thioketal bonds and a precursor of a pharmaceutically active agent. The precursor of the pharmaceutically active agent may be located in the backbone or may be a pendant group. The polymer may degrade in certain environments (e.g., aqueous environments, acidic environments, in vivo, etc.) to produce the pharmaceutically active agent and other biocompatible degradation products, such as certain ketones, alcohols, and/or thiols. Regardless of the location of the precursor of the pharmaceutically active agent in the repeat unit(s), the polymer may have a prolonged degradation time and/or release of the pharmaceutically active agent in certain environments. Various compositions, described herein, may be particularly well suited for applications requiring extended release of pharmaceutically active agents, such as the treatment of ophthalmic disorders.

14 Claims, 9 Drawing Sheets

(56) References Cited

U.S. PATENT DOCUMENTS

2015/0231302 A1 8/2015 Duvall et al.
2016/0000929 A1 1/2016 Ng et al.
2016/0022829 A1 1/2016 Yurkovestskiy et al.

OTHER PUBLICATIONS

Broaders, Synthesis and Evaluation of Environmentally Responsive Polymeric Materials. Dissertation. University of California, Berkeley. Spring 2011. 76 pages.

Guo et al., Extended Release of Native Drug Conjugated in Polyketal Microparticles. J Am Chem Soc. May 18, 2016;138(19):6127-30. doi: 10.1021/jacs.6b02435.

Kao, Local and Sustained Delivery of Hydrophobic Drugs to the Spinal Cord with Polyketal Microparticles. Dissertation. Georgia Institute of Technology. Dec. 2009. 143 pages.

England et al., Polyacetal-stilbene conjugates—The first examples of polymer therapeutics for the inhibition of HIF-1 in the treatment of solid tumours. J Control Release. Dec. 28, 2012;164(3):314-22. doi: 10.1016/j.jconrel.2012.08.017.

Tong et al., Smart chemistry in polymeric nanomedicine. Chem Soc Rev. Jun. 2014;43(20):6982-7012. doi:10.1039/c4cs00133h.

Vicent et al., Polyacetal-diethylstilboestrol: a polymeric drug designed for pH-triggered activation. J Drug Target. Sep. 2004;12(8):491-501.

PCT/US2017/030041, Aug. 14, 2017, International Search Report and Written Opinion.

PCT/US2017/030041, Nov. 8, 2018, International Preliminary Report on Patentability.

\* cited by examiner

FIG. 4A  FIG. 4B  FIG. 4C
Untreated group  Day 4  Day 21
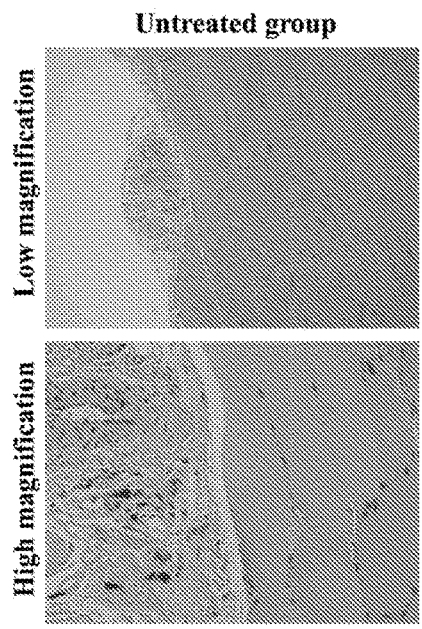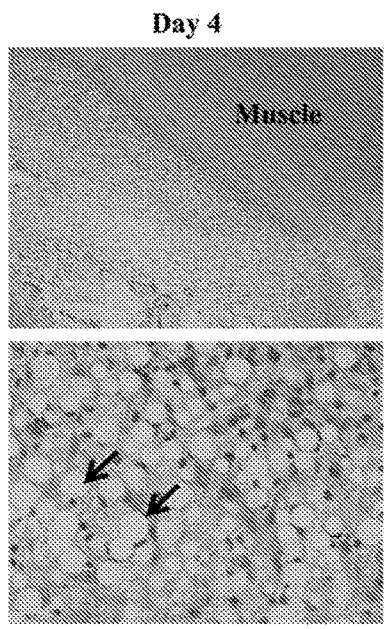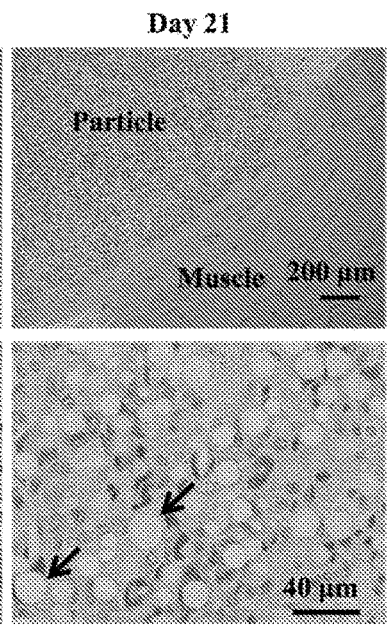
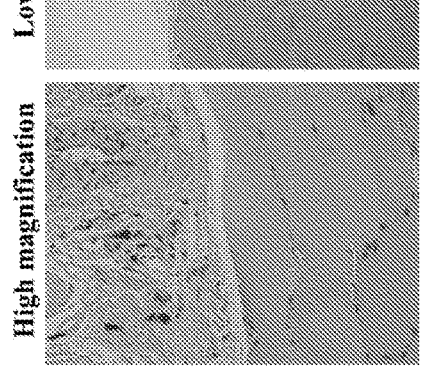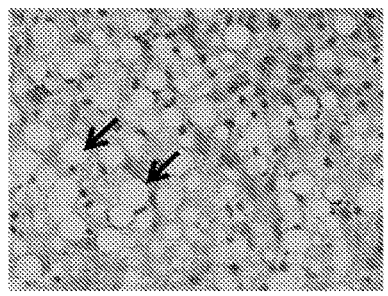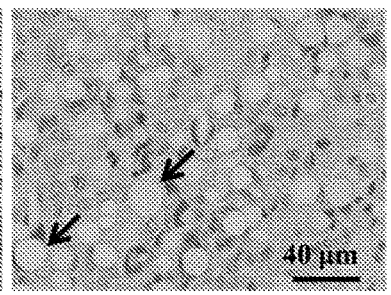
FIG. 4D  FIG. 4E  FIG. 4F FIG. 8A
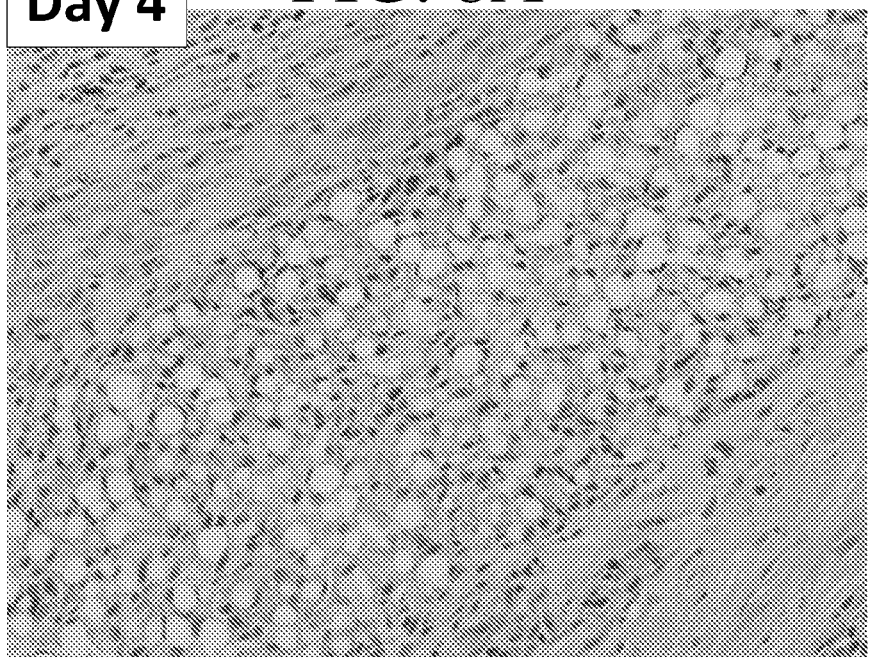
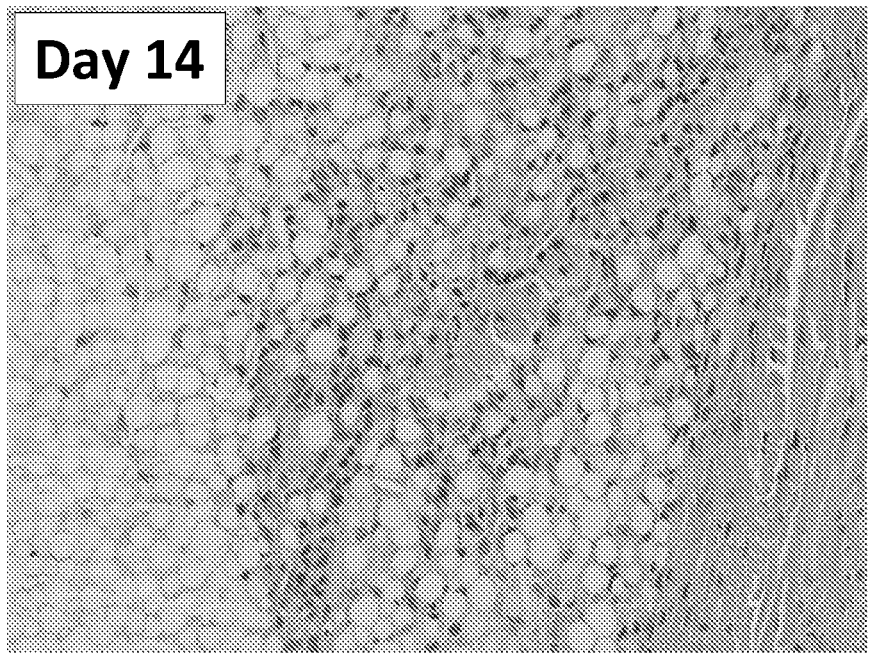
FIG. 8B

POLY(KETALS) AND RELATED COMPOSITIONS AND METHODS

RELATED APPLICATIONS

This application is a national stage filing under 35 U.S.C. § 371 of International Patent Application Serial No. PCT/US2017/030041, filed Apr. 28, 2017, entitled "Poly(Ketals) and Related Compositions and Methods," which claims the benefit of U.S. Provisional Patent Application Ser. No. 62/329,443, filed Apr. 29, 2016, entitled "Poly(Ketals) and Related Compositions and Methods," by Kohane, et al., each of which is incorporated herein by reference in its entirety.

TECHNICAL FIELD

Compositions comprising polymers comprising one or more ketal, monothioketal, and/or thioketal bonds are provided, as well as related methods and kits.

BACKGROUND

Development of biodegradable drug delivery systems which can provide very prolonged (e.g. months) drug release in native form with a minimal initial burst and without undesirable degradation products is advantageous for the treatment of chronic diseases. Polyketals are biomaterials, which can be acid-responsive, biodegradable, and have good biocompatibility, that could have broad applicability in drug delivery and other biomedical applications. However, facile synthesis of high molecular weight polyketals is challenging and short durations of drug release from polyketal particulate formulations limit its application in drug delivery. Accordingly, improved compositions and methods are needed.

SUMMARY

Compositions comprising polymers comprising one or more ketal, monothioketal, and/or thioketal bonds are provided, as well as related methods and kits. The subject matter of the present invention involves, in some cases, interrelated products, alternative solutions to a particular problem, and/or a plurality of different uses of one or more systems and/or articles.

In one set of embodiments, compositions are provided. In one embodiment, a composition comprises a polyketal or salt thereof comprising a repeating unit comprising a precursor of an anti-glaucoma agent.

In another embodiment, a composition comprises a polyketal or salt thereof comprising a repeating unit comprising a precursor of a steroid, prostaglandin, prostaglandin analog, or prostamide.

In yet another embodiment, a composition comprises a polyketal or salt thereof comprising a repeating unit comprising a precursor of a pharmaceutically active agent, wherein the pharmaceutically active agent comprises two or more hydroxyl groups.

In one embodiment, a composition comprises a poly-monothioketal or salt thereof comprising a repeating unit comprising a precursor of a pharmaceutically active agent.

In another embodiments, a composition comprises a poly-thioketal or salt thereof comprising a repeating unit comprising a precursor of a pharmaceutically active agent.

In yet another embodiment, a composition comprises a polymer comprising one or more repeat units of formula (I):

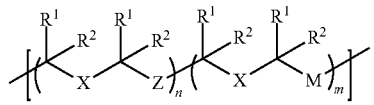

or a salt thereof, wherein:
each $R^1$ and $R^2$ is independently alkyl, optionally substituted;
each Z is independently a precursor of a pharmaceutically active agent;
each X is independently $-L^1-(R^3)_q-L^1-$, wherein each $R^3$ is optionally substituted with 0-5 $T^1$;
each M is independently $-L^2-(R^4)_r-L^2-$, wherein each $R^4$ is optionally substituted with 0-5 $T^2$;
each $R^3$ and $R^4$ is independently alkylene, heteroalkylene, carbocyclylene, heterocyclylene, alkenylene, heteroalkenylene, alkynylene, heteroalkynylene, arylene, or heteroarylene;
each $L^1$ and $L^2$ is independently —O— or —S—;
each $T^1$ and $T^2$ is independently $-R^5$ or $-R^6-Z^2$
each $R^5$ is alkyl, heteroalkyl, alkenyl, heteroalkenyl, heterocyclyl, hydroxyl, halo, thio, oxo, thioxo, amino, $-NO_2$, or acyl, optionally substituted;
each $R^6$ is alkylene, heteroalkylene, alkenylene, heteroalkenylene, —O—, —S—, —N(R)—, or acylene, optionally substituted;
$Z^2$ is a pendant precursor of a pharmaceutically active agent;
R is independently hydrogen or alkyl;
n and m are independently 0-5; and
q and r are independently 1-5;
provided that:
(i) n is greater than 0 and the pharmaceutically active agent comprises two or more hydroxyl groups;
(ii) n is greater than 0 and the pharmaceutically active agent is a steroid, prostaglandin, prostaglandin analog, or a prostamide;
(iii) n is greater than 0 and the pharmaceutically active agent is an anti-glaucoma agent;
(iv) at least one of X, Z, or M comprises —S—; or
(v) n and m are greater than or equal to 1.

In one embodiment, a composition comprises a polymer comprising formula (II):

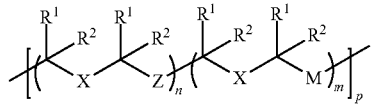

or a salt thereof, wherein:
each $R^1$ and $R^2$ is independently alkyl, optionally substituted;
each Z is independently a precursor of a pharmaceutically active agent;
each X is independently $-L^1-(R^3)_q-L^1-$, wherein each $R^3$ is optionally substituted with 0-5 $T^1$;
each M is independently $-L^2-(R^4)_r-L^2-$, wherein each $R^4$ is optionally substituted with 0-5 $T^2$;
each $R^3$ and $R^4$ is independently alkylene, heteroalkylene, carbocyclylene, heterocyclylene, alkenylene, heteroalkenylene, alkynylene, heteroalkynylene, arylene, or heteroarylene;

each $T^1$ and $T^2$ is independently —$R^5$ or —$R^6$—$Z^2$ each $R^5$ is alkyl, heteroalkyl, alkenyl, heteroalkenyl, heterocyclyl, hydroxyl, halo, thio, oxo, thioxo, amino, —$NO_2$, or acyl, optionally substituted;

each $R^6$ is alkylene, heteroalkylene, alkenylene, heteroalkenylene, —O—, —S—, —N(R)—, or acylene, optionally substituted;

$Z^2$ is a pendant precursor of a pharmaceutically active agent;

each $L^1$ and $L^2$ is independently —O— or —S—;

R is independently hydrogen or alkyl;

n and m are independently 0-5;

q and r are independently 1-5; and p is 3-10,000;

provided that:

(i) n is greater than 0 and the pharmaceutically active agent comprises two or more hydroxyl groups;

(ii) n is greater than 0 and the pharmaceutically active agent is a steroid, prostaglandin, prostaglandin analog, or a prostamide;

(iii) n is greater than 0 and the pharmaceutically active agent is an anti-glaucoma agent;

(iv) at least one of X, Z, or M comprises —S—; or (v) n and m are greater than or equal to 1.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 4A-4F shows hematoxylin-eosin stained sections of the connective tissue and muscle (and mass of particles when present) near the sciatic nerve in untreated animals or at the injection sites at 4 or 21 days in animals injected with 8 mg of DCE microparticles. Arrows indicate the outlines of particles.

FIGS. 8A-8B show hematoxylin-eosin stained sections of the ophthalmic tissue of rats on day 4 and day 14 after subconjunctival injection of microparticles formed from a polymer including repeat units containing a ketal bond and a precursor of Tafluprost acid.

DETAILED DESCRIPTION

Figure 1A:
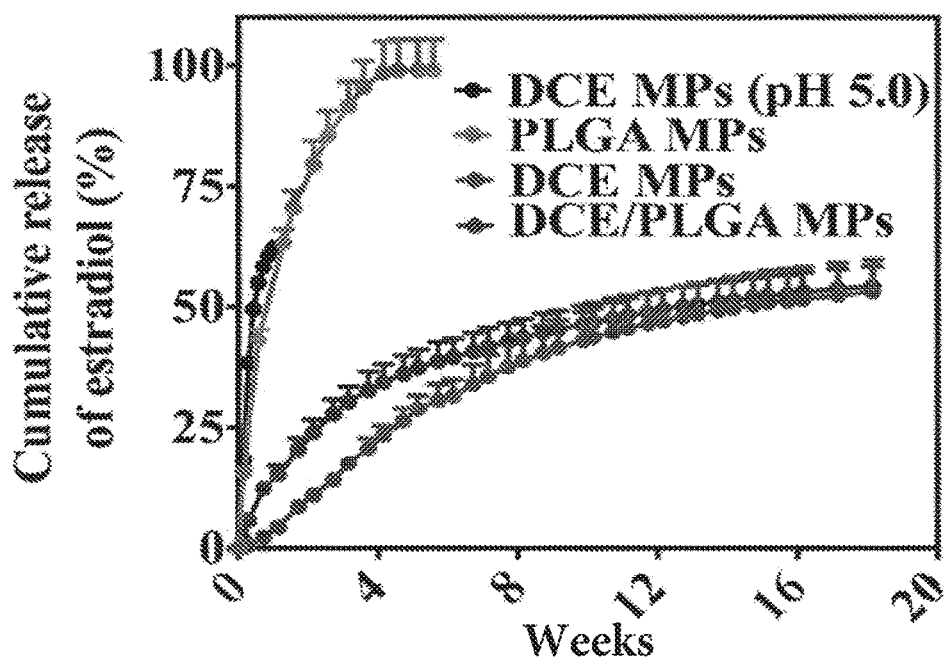
FIG. 1A shows the cumulative release of estradiol (%) from microparticles at 37° C. in PBS having a pH of 7.4 and containing 0.1 wt % Tween 80. The data are means+/−SD; n=4.
Figure 1B:
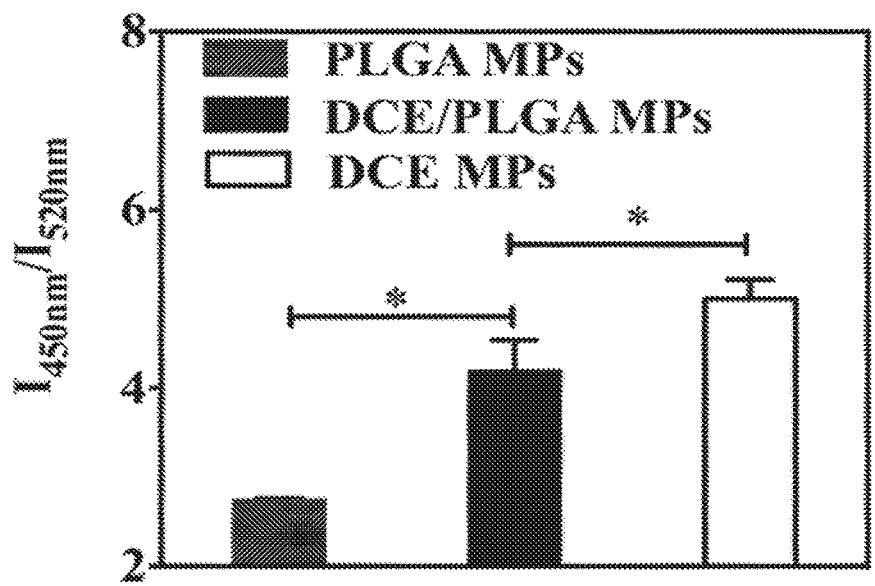
FIG. 1B shows the quantification of the average $I_{450\ nm}/I_{520\ nm}$ in each microparticle type (data are means+/−SD; n=8). * indicates p<0.05.
Figure 2A:
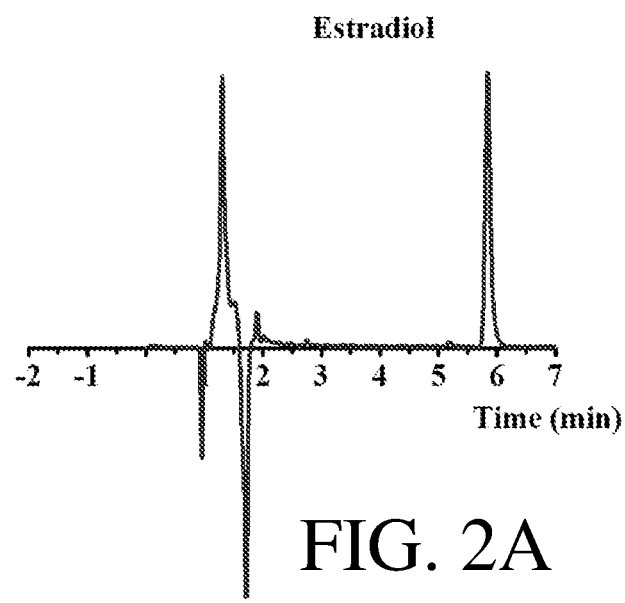
FIGS. 2A-2B show the HPLC chromatograms of pure estradiol and release media of microparticles having a single peak at 5.8 min (arrows). The single peak in the release media demonstrated the absence of oligomers of estradiol conjugate.
Figure 2B:
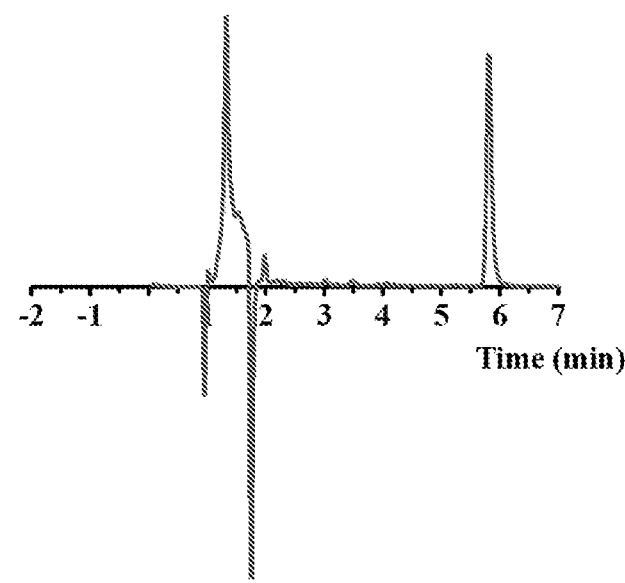
Figure 2C:
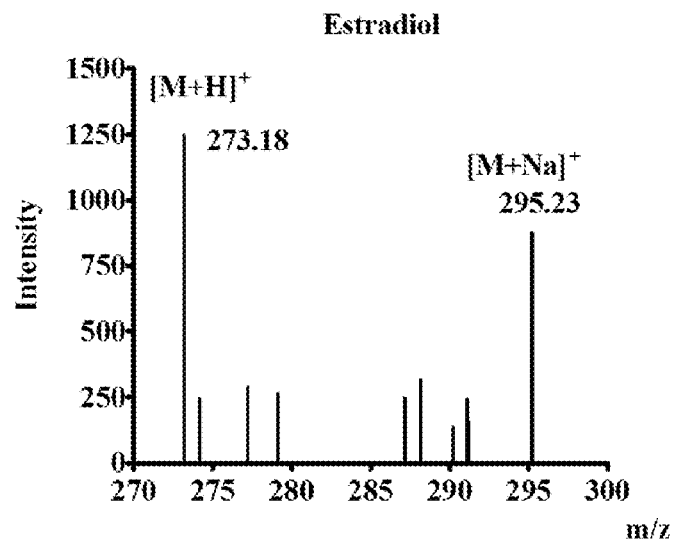
FIGS. 2C-2D show LC-MS chromatograms of pure estradiol and release media of microparticles that confirm the molecular weight (m/z 295.23 is [M+Na]+) observed at ~5.8 min corresponded to that of pure estradiol (left panel).
Figure 2D:
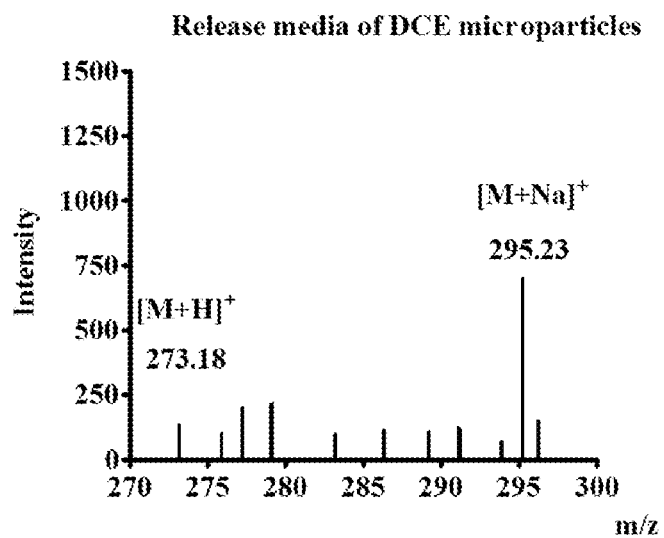

Compositions comprising polymers comprising one or more ketal, monothioketal, and/or thioketal bonds are provided, as well as related methods and kits. In some embodiments, a polymer may comprise one or more repeat units comprising one or more ketal, monothioketal, and/or thioketal bonds and a precursor of a pharmaceutically active agent. The precursor of the pharmaceutically active agent may be located in the backbone or may be a pendant group. The polymer may degrade in certain environments (e.g., aqueous environments, acidic environments, in vivo, etc.) to produce a pharmaceutically active agent and other degradation products (e.g., biocompatible degradation products), such as certain ketones, alcohols, and/or thiols. Regardless of the location of the precursor of the pharmaceutically active agent in the repeat unit(s), the polymer may have a prolonged degradation time and/or release of a pharmaceutically active agent in certain environments. Various compositions, described herein, may be particularly well suited for applications requiring extended release of pharmaceutically active agents, such as the treatment of ophthalmic disorders (e.g., glaucoma).

In one aspect, compositions are provided. In some embodiments, the composition may comprise a polyketal or salt thereof comprising one or more repeat units comprising ketal bonds and a precursor of a pharmaceutically active agent. In some such embodiments, greater than or equal to about 70 mole percent (e.g., greater than or equal to about 75 mol. %, greater than or equal to about 80 mol. %, greater than or equal to about 85 mol. %, greater than or equal to about 90 mol. %, greater than or equal to about 95 mol. %, 100 mol. %) of the hydrolytically degradable and/or biodegradable bonds in the polymer may be ketal bonds. In some embodiments, the polymer comprising ketal bonds may be sensitive to degradation in aqueous environments and/or acidic environments (e.g., pH of less than or equal to about 7.0, pH of less than or equal to about 6.8, pH of less than or equal to about 6.5, pH of less than or equal to about 6.0, pH of less than or equal to about 5.5, pH of less than or equal to about 5.0)

In some embodiments, the pharmaceutically active agent released as a degradation product may be an anti-glaucoma agent. In some instances, the degradation products may comprise a precursor of the precursor of the anti-glaucoma agent, as described in more detail below. In certain embodiments, the anti-glaucoma agent is selected from the group consisting of prostaglandin analogs, beta blockers, alpha agonists, and carbonic anhydrase inhibitors. For instance, the anti-glaucoma agent is selected from the group consisting of tafluprost, bimatoprost, travopost, latanoprost, timolol, unoprostone, tafluprost acid, latanoprost acid, bimatoprost, and bimatoprost acid.

"Precursor," as used herein, means a molecule which, after undergoing loss and/or gain of a ligand, functional group, or the like, and/or undergoing a reaction (e.g., chemical reaction of a functional group), dissociation from a compound, agent, mixture, etc., is a therapeutically active agent effective at treating a subject in need of treatment for a disorder (a subject at risk of, or currently or previously afflicted with the disorder). In some embodiments, a precursor of a pharmaceutically active agent may be formed by reacting one or more functional groups in the pharmaceutically active agent with one or more moieties that will produce a precursor of the precursor of the pharmaceutically active agent having the required functional groups for incorporation into the polymer. In some embodiments, the precursor (or precursor of the precursor) to a pharmaceutically active agent may have diminished or substantially no therapeutic activity relative to the pharmaceutically active agent.

It should be understood that as used herein "degradation" and "degradation products" have their ordinary meaning in the art. Degradation of a polymer may refer to the cleavage of one or more bonds of the polymer to produce polymer fragments as well as the cleavage of bond(s) of the polymer fragments and fragments thereof. For example, a polymer and fragments thereof may undergo one or more cleavages to produce degradation products that are not susceptible to additional bond cleavage in their present environment (e.g., an original monomer, pharmaceutically active agent). In some such cases, these degradation products may be susceptible to additional bond cleavage(s) in a different environment. In another example, a polymer may undergo a few cleavages to produce polymer fragments that are susceptible to additional bond cleavage in the present environment. Degradation products of a polymer may refer to any molecule that is derived from the polymer, including but not limited to molecules that are susceptible to additional bond cleavage(s) in their present environment and molecules that are not susceptible to additional bond cleavage(s) in their present environment.

In certain embodiments, in which the polymer is a polyketal or salt thereof, one or more repeat units comprise one or more ketal bonds and a precursor of a steroid, prostaglandin, prostaglandin analog, or prostamide. In such cases, the pharmaceutically active agent released as a degradation product may be a steroid, prostaglandin, prostaglandin analog, or prostamide. In some instances, the degradation products may comprise a precursor of the precursor of the steroid, prostaglandin, prostaglandin analog, or prostamide.

In certain embodiments, one or more repeat units comprise one or more ketal bonds and a precursor of a steroid, such as a corticosteroid. In some instances, the steroid is selected from the group consisting of estradiol, dexamethasone, prednisone, testosterone, cholic acid, triamcinolone acetonide, triamcinolone, lanosterol, cortisol, and nandrolone.

In certain embodiments, one or more repeat units comprise one or more ketal bonds and a precursor of a prostaglandin. In some such cases, the prostaglandin is selected from the group consisting of dinoprostone, alprostadil, dinoprost, and misoprostol.

In some embodiments, one or more repeat units comprise one or more ketal bonds and a precursor of a prostaglandin analog. In some instances, the prostaglandin analog is selected from the group consisting of travoprost, latanoprost, tafluprost, unoprostone, tafluprost acid, latanoprost acid, and bimatoprost acid.

In some embodiments, the prostaglandin analog is a prostamide. For instance, in certain embodiments, one or more repeat units comprise one or more ketal bonds and a precursor of a prostamide. In some such cases, the prostamide is bimatoprost.

In certain embodiments, in which the polymer is a polyketal or salt thereof, one or more repeat units comprise one or more ketal bonds and a precursor of a pharmaceutically active agent having one, two, three, or more hydroxyl groups (e.g., two hydroxyl groups, three or more hydroxyl groups, four or more hydroxyl groups). For instance, one or more repeat units may comprise one or more ketal bonds and a precursor of a pharmaceutically active agent having two or more hydroxyl groups (e.g., two hydroxyl groups, three or more hydroxyl groups, four or more hydroxyl groups). In some embodiments, the pharmaceutically active agent released as a degradation product may be a pharmaceutically active agent having two or more hydroxyl groups. In certain embodiments, the two or more hydroxyl groups may be used to incorporate the pharmaceutically active agent into the polymer. In some such embodiments, the precursor of the pharmaceutically active agent comprises two or more —O— (e.g., —OH). Non-limiting examples of pharmaceutically active agents having one or more hydroxyl groups (e.g., two or more hydroxyl groups) include, but are not limited to, triamcinolone acetonide, latanoprost, tafluprost, bimatoprost, paclitaxel, travoprost, erythromycin, lankacidin c, lankamycin, dalfopristin, losartan, and doxorubicin.

In some embodiments, the composition may comprise a polymonothioketal comprising one or more repeat units comprising a monothioketal bond and a precursor of a pharmaceutically active agent. In some such embodiments, greater than or equal to about 33 mole percent (e.g., greater than or equal to about 40 mol. %, greater than or equal to about 50 mol. %, greater than or equal to about 60 mol. %, greater than or equal to about 70 mol. %, greater than or equal to about 80 mol. %, greater than or equal to about 90 mol. %, 100 mol. %) of the hydrolytically degradable and/or biodegradable bonds in the polymer may be monothioketal bonds. In some embodiments, the polymer comprising monothioketal bonds may be sensitive to degradation in certain aqueous environments, acidic environments, and in the presence of reactive oxygen species (ROS).

In some embodiments, the pharmaceutically active agent released as a degradation product may comprise one or more thiols. In some such embodiments, the one or more thiol groups may be used to incorporate the pharmaceutically active agent into the polymer. In some such embodiments, the precursor of the pharmaceutically active agent comprises —S— (e.g., —SH). Non-limiting examples of pharmaceutically active agent having one or more thiol groups include, but are not limited to, penicillamine, tiopronin, captopril, and dl-thiorphan, dimercaprol, and largazole thiol. In other embodiments, the pharmaceutically active agent does not comprise one or more thiols groups. In some embodiments, polymonothioketal may also comprise one or more ketal bond.

In some embodiments, the composition may comprise a polythioketal comprising one or more repeat units comprising thioketal bonds and a precursor of a pharmaceutically active agent. In some such embodiments, greater than or equal to about 70 mole percent (e.g., greater than or equal to about 75 mol. %, greater than or equal to about 80 mol. %, greater than or equal to about 85 mol. %, greater than or equal to about 90 mol. %, greater than or equal to about 95 mol. %, 100 mol. %) of the hydrolytically degradable and/or biodegradable bonds in the polymer may be thioketal bonds. In some embodiments, the pharmaceutically active agent released as a degradation product may comprise two or more thiols. In some embodiments, the polymer comprising thioketal bonds may sensitive to degradation in the presence of reactive oxygen species (ROS). In some embodiments, the polymer comprising thioketal bonds may not be sensitive to degradation in certain acidic environments.

In some embodiments, the degradation products may comprise a precursor of the precursor of the pharmaceutically active comprising two or more —S—. In other embodiments, the pharmaceutically active agent released as a degradation product may comprise two or more thiols (e.g., two, three, four, or more). In certain embodiments, the pharmaceutically active agent released as a degradation product may comprise less than two thiols (e.g., one thiol, or no thiols). In some such embodiments, the pharmaceutically active agent may be a pendant group. A non-limiting example of pharmaceutically active agent having two or more thiol groups is dimercaprol.

In general, any suitable pharmaceutically active agents may be incorporated into the polymer in the form of a precursor. Exemplary classes of pharmaceutically active agents that may be incorporated into the polymer in the form of a precursor include anti-glaucoma agents, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, sedatives, opioids, pain-relieving agents, analgesics, anti-pyretics, hormones, prostaglandins, prostaglandin analogues, prostamides, and combinations thereof. In certain embodiments, the pharmaceutically active agent is selected from the group consisting of an anti-cancer agent, an antibiotic, an anti-glaucoma agent, a hormone, and a steroid.

In some embodiments, a suitable pharmaceutically active agent may comprise one or more functional groups (e.g., hydroxyl, thiol, acyl, amino) that allow the pharmaceutically active agent to be used directly or indirectly as monomer in the polymerization reactions, described herein. Direct utilization refers to the ability to use the pharmaceutically active agent without further chemical modification prior to use in the polymerization reactions. For example, a pharmaceutically active agent comprising two or more hydroxyl groups may be directly utilized in the polymerization reactions, described herein. In some such embodiments, the precursor of the pharmaceutically active agent may be in the backbone of the polymer. As another example, a pharmaceutically active agent comprising two or more thiol groups or comprising a thiol group and a hydroxyl group may be directly utilized in the polymerization reactions. In some such cases, the precursor of the pharmaceutically active agent may be in the backbone of the polymer. In one example, a pharmaceutically active agent having one hydroxyl group or thiol group may be directly utilized in the polymerization reactions and may be a pendant group. Indirect utilization refers to the chemical modification of the pharmaceutically active agent prior to use in polymerization reactions. The chemical modification may comprise converting one or more functional groups of the pharmaceutically active agent to one or more hydroxyl or thiol groups or reacting one or more functional groups of the pharmaceutically active agent with a linker to produce one or more free hydroxyl or thiol groups. In some embodiments, the suitable linker may be biocompatible and biodegradable. Those of ordinary skill in the art would be knowledgeable of suitable chemical modification chemistry and linkers based on general knowledge in the field and could readily select suitable chemistry based on the description provided herein.

In some embodiments, the pharmaceutically active agent may be a small molecule. For instances, in some embodiments, the molecular weight of the pharmaceutically active agent and/or the precursor of the pharmaceutically active agent may be greater than or equal to about 50 g/mol and less than or equal to about 1,000 g/mol. In other embodiments, the pharmaceutically active agent may not be a small molecule. Regardless of whether the pharmaceutically active agent is a small molecule, the pharmaceutically active agent may be an organic molecule.

In some embodiments, the polymer may further comprise one or more moiety designed to impart beneficial properties to the polymer. For instance, the polymer may also comprise a reactive oxygen species (ROS) sensitive moiety, a photoactive agent, a hydrophobicity modifier, a hydrophilicity modifier, a cross-linking moiety, second precursor of a second pharmaceutically active agent, or combinations thereof.

In some embodiments, the polymer may also comprise a ROS sensitive moiety. For instance, the polymer may comprise (i) one or more ketal, monothioketal, and/or thioketal bonds, (ii) a precursor of a pharmaceutically active agent, and/or (iii) a ROS sensitive moiety, such as an olefin that is sensitive to a reactive oxygen species. In one embodiment, the ROS sensitive moiety may be —S—C=C—S—, which is sensitive to singlet oxygen. In some embodiments, the ROS sensitive moiety may allow the polymer to more readily degrade in the presence of ROS, e.g., in addition to acidic environments. The ROS sensitive moiety may be in the backbone of one or more repeat units. In general, a reactive oxygen species (ROS) sensitive moiety has its ordinary meaning in the art and may refer to a moiety (e.g., functional group, bond, pendant group) that undergoes a chemical (e.g., cleavage) or physical (e.g., conformational change) in the present of a reactive oxygen species. In some embodiments, the ROS sensitive moiety undergoes a chemical change. In certain cases, the ROS sensitive moiety undergoes a physical change. The ROS sensitive moiety may be in the backbone of the polymer and/or may be a pendant group.

In some embodiments, the polymer may also comprise a photoactive agent. For instance, the polymer may comprise (i) one or more ketal, monothioketal, and/or thioketal bonds, (ii) a precursor of a pharmaceutically active agent, and/or (iii) a photoactive agent, such as a photoacid generator. Photoacid generators release acid upon exposure to certain wavelength of light (e.g., UV light). The acid generated by the photoacid generator may increase the degradation rate of polymers comprising ketal and monothioketal bonds. In one embodiment, the photoacid generator may be a pendant group attached to the repeat unit via an ester linkage. Upon exposure to certain wavelengths of light (e.g., UV light), the ester group will be photolysed to release free acid. Those of ordinary skill in the art would be knowledgeable of such photoacid generators based on ordinary skill in the art. In general, a photoactive agent has its ordinary meaning in the art and may refer to a moiety (e.g., functional group, bond, pendant group) that undergoes a chemical (e.g., cleavage) or physical (e.g., conformational change) in response to electromagnetic radiation at a certain wavelength or range of wavelengths (e.g., UV wavelengths, visible wavelengths). In some embodiments, the photoactive agent undergoes a chemical change. In certain cases, the photoactive agent undergoes a physical change. The photoactive agent may be in the backbone of the polymer and/or may be a pendant group.

In some embodiments, the polymer may also comprise a hydrophobicity or a hydrophilicity modifier designed to alter the hydrophobicity or hydrophilicity of the polymer. For instance, a repeat unit may comprise a relatively long alkyl chain (e.g., $C_{6-20}$ alkyl) or aryl group in the backbone or as a pendant group to increase the hydrophobicity of the polymer. In some such embodiments, the hydrophobicity modifier may function to slow the degradation rate compared to the same polymer lacking the hydrophobicity modifier. Alternatively, a repeat unit may comprise a relatively hydrophilic group, such as one or more ethylene glycol repeat units, to increase the hydrophilicity of the polymer. In some such embodiments, the hydrophilicity modifier may function to increase the degradation rate compared to the same polymer lacking the hydrophilicity modifier.

In some embodiments, the polymer may also comprise one or more cross-linking moieties. For instance, the polymer may comprise (i) one or more ketal, monothioketal, and/or thioketal bonds, (ii) a precursor of a pharmaceutically active agent, and/or (iii) a cross-linking moiety, such as alkenyls, heteroalkenyls, N-hydroxysuccinimide esters, imidoesters, maleimides, thiols, hydroxyls, acyls, acyl-alkenyls (e.g., acrylate, methyl acrylate) amino, and azides. In general, the cross-linking moiety may be any suitable group that is capable of reacting with another moiety (e.g., pendant group, functional group) to form a cross-link. In some instances, a crosslink may be formed by reaction of a pendant cross-linking moiety in one polymer with a pendant group or moiety in the backbone of another polymer. In some embodiments, in which the composition comprises particles formed from the polymers described herein, the cross-linking moiety may be used to cross-link the polymers in the particle.

In some embodiments, the polymer may also comprise a second precursor of a second pharmaceutically active agent. For instance, the polymer may comprise (i) one or more ketal, monothioketal, and/or thioketal bonds, (ii) a precursor of a pharmaceutically active agent, and/or (iii) a second precursor of a second pharmaceutically active agent. The second precursor of the second pharmaceutically active agent may be different from the precursor of the pharmaceutically active agent. In general, the second pharmaceutically active agent may be any suitable pharmaceutically active agent. It should be understood that the description of the precursor of a pharmaceutically active agent may apply to the second precursor of the second pharmaceutically active agent.

In some embodiments, the polymer may have a relatively high weight percentage of the pharmaceutically active agent. In some embodiments, the weight percentage and/or mole percentage of the precursor of the pharmaceutically active agent in the polymer may be greater than or equal to about 1%, greater than or equal to about 3%, greater than or equal to about 5%, greater than or equal to about 10%, greater than or equal to about 20%, greater than or equal to about 30%, greater than or equal to about 40%, greater than or equal to about 50%, greater than or equal to about 60%, or greater than or equal to about 70%. In some instances, the weight percentage and/or mole percentage of the precursor of the pharmaceutically active agent in the polymer may be less than or equal to about 100%, less than or equal to about 90%, less than or equal to about 80%, less than or equal to about 70%, less than or equal to about 60%, or less than or equal to about 50%. All combinations of the above-referenced ranges are possible (e.g., greater than or equal to about 5% and less than or equal to about 100 wt. %; greater than or equal to about 10% and less than or equal to about 80 wt. %; greater than or equal to about 30% and less than or equal to about 80%). In some embodiments, the polymer may comprise or consist essentially of ketal, monothioketal, and/or thioketal bonds, (ii) a precursor of a pharmaceutically active agent, and/or (iii) a second precursor of a second pharmaceutically active agent. For instance, greater than 95 wt. or mol. % of the polymer may comprise or consist essentially of ketal, monothioketal, and/or thioketal bonds, (ii) a precursor of a pharmaceutically active agent, and/or (iii) a second precursor of a second pharmaceutically active agent.

In some embodiments, the polymer may have a relatively high number average molecular weight. For instance, in some embodiments, the number average molecular weight of the polymer is greater than or equal to about 1,000 g/mol, greater than or equal to about 5,000 g/mol, greater than or equal to about 10,000 g/mol, greater than or equal to about 25,000 g/mol, greater than or equal to about 50,000 g/mol, greater than or equal to about 100,000 g/mol, or greater than or equal to about 250,000 g/mol. In some instances, the number average molecular weight of the polymer is less than or equal to about 1,000,000 g/mol, less than or equal to about 750,000 g/mol, less than or equal to about 500,000 g/mol, less than or equal to about 250,000 g/mol, less than or equal to about 100,000 g/mol, or less than or equal to about 50,000 g/mol. All combinations of the above-referenced ranges are possible (greater than or equal to about 1,000 g/mol and less than or equal to about 1,000,000 g/mol; greater than or equal to about 5,000 g/mol and less than or equal to about 250,000 g/mol; greater than or equal to about 10,000 g/mol and less than or equal to about 250,000 g/mol; greater than or equal to about 25,000 g/mol and less than or equal to about 250,000 g/mol).

It should be understood that the polymer molecules are generally extended molecular structures comprising backbones which optionally contain pendant side groups, wherein the term backbone is given its ordinary meaning as used in the art, e.g., a linear chain of atoms within the polymer molecule by which other chains may be regarded as being pendant (e.g., the longest continuous bond pathway of the polymer). Typically, but not always, the backbone is the longest chain of atoms within the polymer. A polymer may be a regular (e.g., homopolymer) or irregular (e.g., copolymer, for example, a block, alternating, or random copolymer). A polymer may also comprise a mixture of polymers. In some embodiments, the polymer may be acyclic or cyclic. A polymer may be cross-linked, for example through covalent bonds, ionic bonds, hydrophobic bonds, and/or metal binding. In some embodiments, a polymer may have a structure of which essentially comprises repeat units derived, actually or conceptually, from molecules of low relative molecular mass (e.g., monomers).

In some embodiments, the polymer may be an irregular polymer. For instance, in some embodiments, the polymer comprising one or more ketal, monothioketal, and/or thioketal bonds and a precursor of a pharmaceutically active agent may be a copolymer, such as a block, alternating, or random copolymer. For example, the polymer may be a block copolymer comprising a polyketal block and another block, such as a polyethylene glycol (PEG) block. Irregular polymers may be used to form a variety of structures, including micelles and bilayers.

In some embodiments, regardless of whether the polymer is regular or irregular, the polymer comprising or more ketal, monothioketal, and/or thioketal bonds and a precursor of a pharmaceutically active agent may comprise greater than or equal to about 3, greater than or equal to about 5, greater than or equal to about 8, greater than or equal to about 10, greater than or equal to about 20, greater than or equal to about 35, greater than or equal to about 50, greater than or equal to about 75, greater than or equal to about 100, greater than or equal to about 250, greater than or equal to about 500, or greater than or equal to about 1,000 ketal, monothioketal, and/or thioketal bonds.

In some embodiments, the polymer comprising one or more ketal, monothioketal, and/or thioketal bonds and a precursor of a pharmaceutically active agent may have the following structures. In one embodiment, the composition, comprising a polymer comprising one or more repeat units of formula (I):

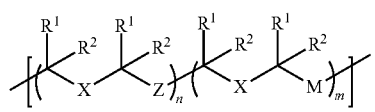

or a salt thereof, wherein:

each $R^1$ and $R^2$ is independently alkyl, optionally substituted;

each Z is independently a precursor of a pharmaceutically active agent;

each X is independently $-L^1-(R^3)_q-L^1-$, wherein each $R^3$ is optionally substituted with 0-5 $T^1$;

each M is independently $-L^2-(R^4)_r-L^2-$, wherein each $R^4$ is optionally substituted with 0-5 $T^2$;

each $R^3$ and $R^4$ is independently alkylene, heteroalkylene, cycloalkylene, heterocycloalkylene, alkenylene, heteroalkenylene, alkynylene, heteroalkynylene, arylene, or heteroarylene;

each $L^1$ and $L^2$ is independently —O— or —S—;

each $T^1$ and $T^2$ is independently —$R^5$ or —$R^6$—$Z^2$ each $R^5$ is alkyl, heteroalkyl, alkenyl, heteroalkenyl, heterocycloalkyl, hydroxyl, halo, thio, oxo, thioxo, amino, —$NO_2$, or acyl, optionally substituted;

each $R^6$ is alkylene, heteroalkylene, alkenylene, heteroalkenylene, —O—, —S—, —N(R)—, or acylene, optionally substituted;

$Z^2$ is a pendant precursor of a pharmaceutically active agent;

R is independently hydrogen or alkyl;

n and m are independently 0-5; and q and r are independently 1-5.

In some embodiments, the polymer may comprise one or more repeat units of formula (I) provided that (i) n is greater than 0 and the pharmaceutically active agent comprises two or more hydroxyl groups; (ii) n is greater than 0 and the pharmaceutically active agent is a steroid, prostaglandin, prostaglandin analog, or a prostamide; (iii) n is greater than 0 and the pharmaceutically active agent is an anti-glaucoma agent; (iv) at least one of X, Z, or M comprises —S—; or (v) n and m are greater than or equal to 1. In some embodiments, $T^1$ and $T^2$ are $R^5$.

In certain embodiments, the polymer comprises two or more (e.g., two, three or more, four or more, etc.) different repeat units of formula (I). In other embodiments, the polymer has one repeat unit of formula (I).

In some embodiments, the repeat units of formula (I) may comprise a relatively high weight or mole percentage of the polymer. For instance, the polymer comprises less than or equal to about 20 wt. % (e.g., less than or equal to about 15 wt. %, less than or equal to about 10 wt. %, less than or equal to about 8 wt. %, less than or equal to about 5 wt. %, less than or equal to about 3 wt. %, less than or equal to about 1 wt. %, less than or equal to about 0.5 wt. %, less than or equal to about 0.1 wt. %, less than or equal to about 0.01 wt. %) and/or 20 mol. % (e.g., less than or equal to about 15 mol. %, less than or equal to about 10 mol. %, less than or equal to about 8 mol. %, less than or equal to about 5 mol. %, less than or equal to about 3 mol. %, less than or equal to about 1 mol. %, less than or equal to about 0.5 mol. %, less than or equal to about 0.1 mol. %, less than or equal to about 0.01 mol. %) of a repeat unit having a structure of a different formula. In instances, the polymer comprises greater than or equal to about 0.01 wt. % and less than or equal to about 20 wt. % (greater than or equal to about 0.01 wt. % and less than or equal to about 10 wt. %, greater than or equal to about 0.01 wt. % and less than or equal to about 5 wt. %, greater than or equal to about 0.01 wt. % and less than or equal to about 1 wt. %) and/or greater than or equal to about 0.01 mol. % and less than or equal to about 20 mol. % (greater than or equal to about 0.01 mol. % and less than or equal to about 10 mol. %, greater than or equal to about 0.01 mol. % and less than or equal to about 5 mol. %, greater than or equal to about 0.01 mol. % and less than or equal to about 1 mol. %) of a repeat unit having a structure of a different formula. In some embodiments, the polymer comprises 0 wt. % or 0 mol. % of a repeat unit having a structure of a different formula.

In some embodiments, the composition comprising a polymer comprising formula (II):

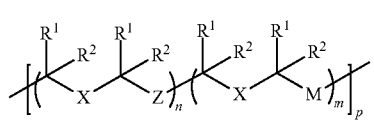

or a salt thereof, wherein:

$R^1$, $R^2$, Z, X, M, n, and m are as described herein; and p is 3-100,000;

In some embodiments, the polymer may comprise formula (II) provided that (i) n is greater than 0 and the pharmaceutically active agent comprises two or more hydroxyl groups; (ii) n is greater than 0 and the pharmaceutically active agent is a steroid, prostaglandin, prostaglandin analog, or a prostamide; (iii) n is greater than 0 and the pharmaceutically active agent is an anti-glaucoma agent; (iv) at least one of X, Z, or M comprises —S—; or (v) n and m are greater than or equal to 1.

In some embodiments, formula (II) may comprise a relatively high weight or mole percentage of the polymer.

For instance, greater than or equal to about 80 wt. % (e.g., greater than or equal to about 85 wt. %, greater than or equal to about 90 wt. %, greater than or equal to about 95 wt. %, greater than or equal to about 97 wt. %, greater than or equal to about 99 wt. %) or greater than or equal to about 80 mol. % (e.g., greater than or equal to about 85 mol. %, greater than or equal to about 90 mol. %, greater than or equal to about 95 mol. %, greater than or equal to about 97 mol. %, greater than or equal to about 99 mol. %) of the polymer consists of formula (II). In instances, greater than or equal to about 85 wt. % and less than or equal to about 100 wt. % (greater than or equal to about 85 wt. % and less than or equal to about 99 wt. %,) and/or greater than or equal to about 85 mol. % and less than or equal to about 100 mol. % (greater than or equal to about 85 mol. % and less than or equal to about 99 mol. %) of the polymer consists of formula (II).

In some embodiments, the polymer has the structure:

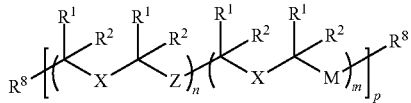

(III)

or a salt thereof, wherein:
$R^1$, $R^2$, Z, X, M, n, m, and p are as described herein;
each $R^8$ is independently —OH, —SH, or

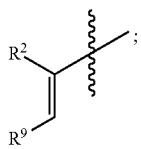

and
each $R^9$ is independently hydrogen or alkyl.

In some embodiments, $R^9$ may be $C_{1-5}$ alkyl (e.g., $C_{1-3}$ alkyl, $C_{1-2}$ alkyl, methyl). In some instances, $R^9$ is hydrogen.

As noted above, the polymer may have a relatively high molecular weight. In some embodiments, p may be 3-100,000; 3-75,000; 3-50,000; 3-25,000; 3-10,000; 3-5,000; 3-1,000; 3-500; 3-100; 5-100,000; 5-75,000; 5-50,000; 5-25,000; 5-10,000; 5-5,000; 5-1,000; 5-500; 5-100; 10-100,000; 10-75,000; 10-50,000; 10-25,000; 10-10,000; 10-5,000; 10-1,000; 10-500; 10-100; 20-100,000; 20-75,000; 20-50,000; 20-25,000; 20-10,000; 20-5,000; 20-1,000; 20-500; or 20-100.

In some embodiments, Z of formula (I), (II), and (III) has the structure:

-T-$Z^1$-T-, wherein:
$Z^1$ is a portion of the pharmaceutically active agent;
T is -$L^3$- or -$L^3$-$(R^7)_t$—;
$L^3$ is —O— or —S—;
$R^7$ is alkylene, heteroalkylene, alkenylene, heteroalkenylene, —O—, —S—, —N(R)—, or acylene, optionally substituted; and
each t is independently 0-5.

In some embodiments, in which the pharmaceutically active agent is used directly in the polymerization reactions, such as those described herein, T is -$L^3$- and $Z^1$ is a portion of the pharmaceutically active agent. In some such embodiments, the pharmaceutically active agent comprises one or more (e.g., one, two or more, three or more, etc.) hydroxyl groups and/or thiol groups as described above. For instance, the pharmaceutically active agent may have the structure H-$L^3$-$Z^1$-$L^3$-H and the precursor of the pharmaceutically active agent may have the structure -$L^3$-$Z^1$-$L^3$-.

In certain embodiments, in which the pharmaceutically active agent undergoes chemical modification prior to utilization in the polymerization reactions, at least one (e.g., one, two, three, etc.) T is independently -$L^3$-$(R^7)_t$— and $Z^1$ is a portion of the pharmaceutically active agent. In some embodiments, the chemical modification may result in the formation of the $L^3$-$R^7$ bond and/or the $R^7$—$Z^1$. For instance, the pharmaceutically active agent may have the structure H—$Z^1$—H and the precursor of the precursor of the pharmaceutically active agent may have the structure H-$L^3$-$R^7$—$Z^1$—$R^7$-$L^3$-H. The precursor of the pharmaceutically active agent may has the structure -$L^3$-$R^7$-$Z^1$—$R^7$-$L^3$-. In certain embodiments, $R^7$ is alkylene, heteroalkylene, —O—, —S—, —N(R)—, or acylene, optionally substituted.

In some embodiments, t is 1-5, 1-4, 1-3, 1-2, or 2-3. In some instances, t is 2. In some such embodiments, -$L^3$-$R^7$—$R^7$—$Z^1$— is -$L^3$-alkylene-acylene-$Z^1$—, -$L^3$-alkylene-O—$Z^1$—, -$L^3$-alkylene-S—$Z^1$—, or -$L^3$-alkylene-N(R)-$Z^1$—, optionally substituted.

In some embodiments, n may be 0-5, 0-4, 0-3, 0-2, 0-1, 1-5, 1-4, 1-3, 1-2, 2, 1, or 0. In certain embodiments n is greater than 0 (e.g., 1, 2). In some such embodiments, the pharmaceutically active agent may be as described above with respect to the polyketal. For instance, the pharmaceutically active agent may comprise two or more hydroxyl groups, as described above. In another example, the pharmaceutically active agent is a steroid, prostaglandin, prostaglandin analog, or a prostamide, as described above. In one example, the pharmaceutically active agent is an anti-glaucoma agent.

In some embodiments, when n is greater than 0, m is 0 as described in more detail below. In other embodiments, n and m are both greater than or equal to 1. In some such embodiments, n and m may be equal. In other embodiments, the ratio of n to m may be 1:2, 1:3, 1:4, 1:5, 2:1, or 3:1.

In some embodiments, for a repeat unit of formula (I), a polymer comprising formula (II), and/or a polymer comprising formula (III), at least one of X, Z, or M comprises —S—. In certain embodiments, the —S— may be part of a monothioketal or thioketal bond. In some such cases, at least one of $L^1$, $L^2$, or $L^3$ is —S—. In some instances, at least one $L^2$ is —S—. In certain instances, at least one $L^3$ is —S—. In some cases, at least one $L^2$ and at least one $L^3$ is —S—. In certain cases, $L^2$ is —S— and/or $L^3$ is —S—. In certain embodiments, $L^1$, $L^2$, and $L^3$ is —S—.

In certain embodiments, for a repeat unit of formula (I), a polymer comprising formula (II), and/or a polymer comprising formula (III), at least one of X, Z, or M comprises —O—. In some embodiments, at least one of $L^1$, $L^2$, or $L^3$ is —O—. In some cases, at least one $L^1$ is —O—. In certain instances, at least one $L^2$ is —O— and/or at least one $L^3$ is —O—. In some instances, at least one $L^1$ and at least one $L^3$ is —O—. In certain cases, $L^1$ is —O—. In some cases, $L^2$ may be —O— and/or $L^3$ is —O—. In some embodiments, $L^2$ and $L^3$ is —O— or $L^1$ and $L^3$ is —O—. In certain embodiments, $L^1$, $L^2$, and $L^3$ is —O—.

In some embodiments, at least one of X, Z, or M comprises —O— and at least one of X, Z, or M comprises —S—. In some such embodiments, a repeat unit of formula (I), a polymer of formula (II), and/or polymer of formula (III) may comprise one or more monothioketal bonds.

In some embodiments, each $R^1$ is independently $C_{1-10}$ alkyl. For instance, each $R^1$ may independently be $C_{1-8}$ alkyl, $C_{1-5}$ alkyl, $C_{1-3}$ alkyl, or $C_{1-2}$ alkyl. In certain embodiments, $R^1$ is methyl.

In some embodiments, each $R^2$ is independently $C_{1-5}$ alkyl (e.g., $C_{1-3}$ alkyl, $C_{1-2}$ alkyl). In certain embodiments, $R^2$ is methyl. In some instances, $R^1$ may independently be $C_{1-8}$ alkyl, $C_{1-5}$ alkyl, $C_{1-3}$ alkyl, or $C_{1-2}$ alkyl and $R^2$ may be independently $C_{1-5}$ alkyl, $C_{1-3}$ alkyl, or $C_{1-2}$ alkyl. In some cases, $R^1$ and $R^2$ are the same. In certain instances, $R^1$ and $R^2$ are the different. In some instances, $R^1$ and $R^2$ may be methyl.

In some embodiments, at least one $R^3$ and $R^4$ may be the backbone anchor for a pendant precursor to a pharmaceutically active agent and/or may comprise the one or more moieties designed to impart beneficial properties to the polymer, as described above. For instance, at least one $R^3$ and $R^4$ may comprise a reactive oxygen species (ROS) sensitive moiety, a photoactive agent, a hydrophobicity modifier, a hydrophilicity modifier, a cross-linking moiety, or second precursor of a second pharmaceutically active agent. For example, in some such embodiments, at least one of $R^3$ and $R^4$ is substituted with $R^5$. For instance, $R^5$ may be a cross-linking moiety such as —SH, —OH, or heteroalkenyl. In some embodiments, $R^5$ may be optionally substituted with a cross-linking moiety (e.g., —$N_3$). $R^3$ and $R^4$ may be substituted with $R^5$, such that X or M, respectively, comprises one, two, three, or four cross-linking moieties. In other embodiments, $R^3$ and $R^4$ do not comprise one or more moieties designed to impart beneficial properties as described above.

In some embodiments, at least one of $R^3$ and $R^4$ is substituted with —$R^6$—$Z^2$, wherein $Z^2$ is the pendant precursor to a pharmaceutically active agent. In some such embodiments, the pharmaceutically active agent may comprise at least one hydroxyl or thiol group. In embodiments in which n is 0, at least one (one, two or more, three or more) of $R^3$ and $R^4$ is substituted with —$R^6$—$Z^2$. In other embodiments, $R^3$ and $R^4$ are not substituted with $R^6$—$Z^2$.

In certain embodiments, embodiments, each $R^3$ and $R^4$ is independently alkylene, heteroalkylene, heteroalkenyl, cycloalkylene, heterocycloalkylene, or arylene, optionally substituted with 0-5 (e.g., 0, 0-4, 0-3, 0-2, 0-1, 1, 1-3, 1-2) $T^1$ or 0-5 (e.g., 0, 0-4, 0-3, 0-2, 0-1, 1, 1-3, 1-2) $T^2$, respectively. In some embodiments, q and r are independently 1-5, 1-4, 1-3, 1-2, 1, 2, or 3.

In some embodiments, X and M are the same or substantially similar. For instance, in some embodiments, $L^1$-$(R^3)_q$-$L^1$- and -$L^2$-$(R^4)_r$-$L^2$- are the same. In another example, —$(R^3)_q$— and —$(R^4)_r$— are the same. In other embodiments, X and M may be different. In certain embodiments, X and/or M comprise a reactive oxygen species (ROS) sensitive moiety, a photoactive agent, a hydrophobicity modifier, a hydrophilicity modifier, a cross-linking moiety (e.g., pendant cross-linking group), and/or second precursor of a second pharmaceutically active agent. In some embodiments, X is independently $L^1$-alkylene-$L^1$, -$L^1$-heteroalkylene-$L^1$, or $L^1$-heteroalkenylene-$L^1$, optionally substituted with 0-5 $T^1$. In some cases, X is -$L^1$-alkylene-cycloalkylene-alkylene-$L^1$- or -$L^1$-alkylene-arylene-alkylene-$L^1$-, optionally substituted with 0-5 $T^1$. In certain embodiments, M is independently $L^2$-alkylene-$L^2$, -$L^2$-heteroalkylene-$L^2$, or $L^2$-heteroalkenylene-$L^2$ optionally substituted with 0-5 $T^2$. In certain cases, M is -$L^2$-alkylene-cycloalkylene-alkylene-$L^2$- or -$L^2$-alkylene-arylene-alkylene-$L^2$-, optionally substituted with 0-5 $T^2$.

As noted above, in some embodiments n is greater than 0. In certain embodiments, n is greater than 0 and m is 0. In some such embodiment, the polymer of formula (II) and the polymer of formula (III) may comprise p repeats of the repeat unit of formula (I) as illustrated below. In such embodiments, a repeat unit of formula (I) has the structure:

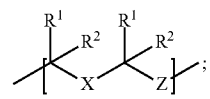

the polymer of formula (II) has the structure:

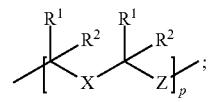

and/or
the polymer of formula (III) has the structure:

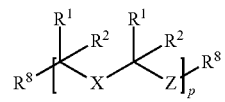

wherein $R^1$, $R^2$, $R^8$, X, p, and Z are defined as described herein.

In certain embodiments, a repeat unit of formula (I) has the structure:

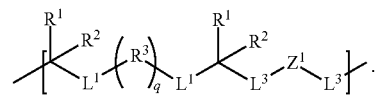

wherein $R^1$, $R^2$, $R^3$, $L^1$, $L^3$, q, and $Z^1$ are defined as described herein.

In certain embodiments, a repeat unit of formula (I) has the structure:

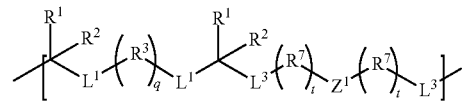

wherein $R^1$, $R^2$, $R^3$, $R^7$, $L^1$, $L^3$, q, t, and $Z^1$ are defined as described herein. In some instances, t is 1-5. In certain cases, one t is 0 and one t is 1-5. In certain embodiments, $R^7$ is alkylene, heteroalkylene, —O—, —S—, —N(R)—, or acylene, optionally substituted. In some embodiments, at least one t is 2 and -$L^3$-$R^7$—$R^7$—$Z^1$— is -$L^3$-alkylene-acylene-$Z^1$—, -$L^3$-alkylene-O—$Z^1$—, -$L^3$-alkylene-S—$Z^1$—, or -$L^3$-alkylene-N(R)—$Z^1$—, optionally substituted.

In some embodiments, n and m may be greater than 0. For instance n and m may be 1-2. In other embodiments, m may be greater than 0 and n may be 0. In some such embodiment, the polymer of formula (II) and the polymer of formula (III) may comprise p repeats of the repeat unit of formula (I). In such embodiments, a repeat unit of formula (I), and accordingly the repeat unit in formula (II) and (III) has the structure:

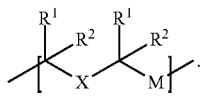

wherein $R^1$, $R^2$, X, and M are defined as described herein.

In certain embodiments, a repeat unit of formula (I) has the structure:

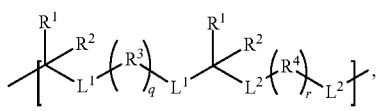

wherein $R^1$, $R^2$, $R^3$, $R^4$, $L^1$, $L^2$, q, $T^1$, $T^2$, $R^6$, $Z^2$ and r are defined as described herein, provided that at least one $R^3$ is substituted with $T^1$, wherein $T^1$ is $R^6$—$Z^2$; and/or at least one $R^4$ is substituted with $T^2$, wherein $T^2$ is $R^6$—$Z^2$. In some such embodiments, the pharmaceutically active agent has less than 2 hydroxyl groups or less than two thiol groups. In certain cases, the combined total of hydroxyl and thiol groups in the pharmaceutically active agent is less than 2.

In some embodiments, for a repeat unit of formula (I) or a polymer comprising formula (II) or formula (III):

each $R^1$ and $R^2$ is independently $C_{1-2}$ alkyl;

each X is independently -$L^1$-$(R^3)_q$-$L^1$-, wherein each $R^3$ is optionally substituted with 0-3 $T^1$;

each M is independently -$L^2$-$(R^4)_r$-$L^2$-, wherein each $R^4$ is optionally substituted with 0-3 $T^2$;

each $R^3$ and $R^4$ is independently alkylene, heteroalkylene, cycloalkylene, heterocycloalkylene, heteroalkenylene, arylene, or heteroarylene;

R is independently hydrogen;

n and m are independently 0-2; and q and r are independently 1-3;

In another aspect of the invention, particles are provided. In some embodiments, the composition may comprise particles comprising any of the polymers described herein. For instance, the particles may be formed from the polymers described herein. In certain embodiments, the particles may comprise a relatively high weight percentage of the polymers, described herein. For instance, polymers of formula (II) or (III) may be greater than 90 wt. % of the total amount of polymers in the particles. In other embodiments, the particles may comprise a second polymer. In general, the second polymer may be any suitable biocompatible and biodegradable polymer. Non-limiting examples include polyesters (e.g., poly(lactic-co-glycolic acid), poloxamer, polyvinyl alcohol (PVA), poly(N-vinylpyrrolidone) (PVP), and polyethylene glycol (PEG).

In some embodiments, the particles may have a relatively large diameter that allows for retention in certain tissue sites (e.g., ocular tissue). For instance, in some embodiments, the particles are microparticles. In certain embodiments, the particles may have an average characteristic dimension of less than 1 mm. For instance, in some embodiments, the average characteristic dimension of the particles is less than about 1,000 microns, less than or equal to about 500 microns, less than or equal to about 100 microns, less than or equal to about 50 microns, less than or equal to about 10 microns, or less than or equal to about 5 microns and greater than or equal to about 1 micron. In certain embodiments, the average characteristic dimension of the particles is greater than or equal to about 5 microns and less than or equal to about 30 microns (e.g., greater than or equal to about 5 microns and less than or equal to about 25 microns, greater than or equal to about 8 microns and less than or equal to about 20 microns, greater than or equal to about 5 microns and less than or equal to about 15 microns).

In other embodiments, the particles may have a relatively small diameter. In certain embodiments, the particles are nanoparticles. For instance, in some embodiments, the average characteristic dimension of the particles is less than about 1,000 nm, less than or equal to about 800 nm, less than or equal to about 600 nm, less than or equal to about 500 nm, less than or equal to about 400 nm, less than or equal to about 300 nm, less than or equal to about 200 nm, less than or equal to about 100 nm, or less than or equal to about 50 nm. In some instances, the average characteristic dimension of the particles is between about 10 nm and about 800 nm, between about 10 nm and about 600 nm, between about 10 nm and about 500 nm, between about 10 nm and about 400 nm, between about 10 nm and about 300 nm, between about 10 nm and about 200 nm, or between about 10 nm and about 100 nm. In some instances, the particles have a diameter less than or equal to 100 nm. In certain cases, the characteristic dimension of the particles is between about 10 nm and about 100 nm.

In some cases, the particles may have a narrow distribution in a characteristic dimension. For instance, in certain embodiments, the coefficient of variation of a characteristic dimension of the particles may be less than or equal to about 20%, less than or equal to about 15%, less than or equal to about 10%, or less than or equal to about 5%.

In some embodiments, the particles may be biocompatible. For instance, in some embodiments, addition of the particles to cells in vitro results in less than 20% cell death, less than or equal to about 15% cell death, less than or equal to about 12% cell death, less than or equal to about 10% cell death, less than or equal to about 8% cell death, less than or equal to about 5% cell death, less than or equal to about 3% cell death, less than or equal to about 2% cell death, or less than or equal to about 1% cell death and their administration in vivo does not induce inflammation or other such adverse effects.

In general, the particles are biodegradable. Biodegradable particles, when introduced into cells, are usually broken down by the cellular machinery or by hydrolysis into components that the cells can either reuse or dispose of without significant toxic effects on the cells (i.e., fewer than about 20% of the cells are killed when the components are added to cells in vitro). The components preferably do not cause adverse effects in vivo. In certain embodiments, the chemical reactions relied upon to break down the biodegradable particles are catalyzed.

The particle may degrade over hours to days to weeks to months to years, thereby releasing the agent (e.g., pharmaceutically active agent, precursor of a pharmaceutically active agent) over an extended period of time. In certain embodiments, the half-life of the particles under physiological conditions is 24-169 hours (e.g., 24-169 hours, 48-169 hours). In certain embodiments, the half-life of the particle under physiological conditions is 7-14 days. In other embodiments, the half-life is from 2-12 weeks. In other embodiments, the half-life is approximately 2-6 months. In other embodiments, the half-life is approximately half a year to six years.

In some embodiments, the particles may release the agent under physiological conditions over an extended period of time. For instance, a composition comprising the particles may release the agent (e.g., at a therapeutically effective amount) for greater than or equal to about 1 day, greater than or equal to about 3 day, greater than or equal to about 7 day, greater than or equal to about 10 days, greater than or equal to about 14 days, greater than or equal to about 30 days, greater than or equal to about 60 days, greater than or equal to about 90 days, greater than or equal to about 120 days, greater than or equal to about 180 days, greater than or equal to about 240 days, greater than or equal to about 300 days, greater than or equal to about 1 year, greater than or equal to about 1.5 years, greater than or equal to about 2 years, greater than or equal to about 2.5 years, greater than or equal to about 3 years, greater than or equal to about 3.5 years, greater than or equal to about 4 years, or greater than or equal to about 4.5 years. In some embodiments, a composition comprising the particles may release the agent (e.g., at a therapeutically effective amount) for less than or equal to about 6 years, less than or equal to about 5.5 years, less than or equal to about 5 years, less than or equal to about 4.5 years, less than or equal to about 4 years, less than or equal to about 3.5 years, less than or equal to about 3 years, less than or equal to about 2.5 years, less than or equal to about 2 years, less than or equal to about 1.5 years, less than or equal to about 1 years, or less than or equal to about 0.5 years. All combinations of the above-referenced ranges are possible (e.g., greater than or equal to about 1 day and less than or equal to about 5 years; greater than or equal to about 30 days and less than or equal to about 5 years; greater than or equal to about 180 days and less than or equal to about 5 years).

In some embodiments, the particle may optionally contain other components (e.g., one or more chemical compounds) in addition to the one or more polymers. For example, the particle may comprise lipids, and/or surfactants. In some embodiments, the other components are not attached to the surface of the particle. In certain embodiments, the other components are included at low concentrations.

In some embodiments, after drying, the particles may form a powder. The powder may be a flowable and/or pillable powder.

In another aspect, the polymers described herein may be used to form a material (e.g., implant) having any suitable shape, e.g., a slab, a disc, a cylinder, a rod, or a ring that can be implanted in a subject via any suitable means (e.g., injection). In some cases, the material can be incorporated into tissues within the subject, e.g., without eliciting any undesirable local or systemic effects, or such that any biological response by the subject does not substantially affect the ability of the material from continuing to function for its intended use. In some embodiments, the material may be implanted in a subject for an extended period of time, e.g., at least about a month, at least about 6 months, or at least about a year.

In one aspect, methods of forming a polymer are provided. In some embodiments, the method comprises reacting monomers of formula (IV):

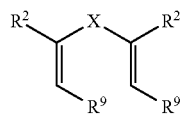

(IV)

with monomers of formula (V):

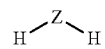

(V)

and/or formula (VI):

(VI)

under suitable conditions to form a polymer of formula (II) or formula (III), wherein $R^2$, $R^9$, M, Z, and X are defined as described herein. In some embodiments, the monomer of formula (V) is a pharmaceutically active agent or a precursor thereof. In certain embodiments, the monomer of formula (IV) may comprise a pendant precursor of a pharmaceutically active agent, a reactive oxygen species (ROS) sensitive moiety, a photoactive agent, a hydrophobicity modifier, a hydrophilicity modifier, or a cross-linking moiety. In certain embodiments, the monomer of formula (VI) may comprise a pendant precursor of a pharmaceutically active agent, a reactive oxygen species (ROS) sensitive moiety, a photoactive agent, a hydrophobicity modifier, a hydrophilicity modifier, or a cross-linking moiety.

In some embodiments, the monomers of formula (IV) and formula (V) and/or (VI) are reacted in the presence of a Lewis acid. In some instances, the Lewis acid is p-toluenesulfonic acid or pyridinium p-toluenesulfonate. The mole percentage of the Lewis acid by mole of monomers may be greater than or equal to about 0.001% and less than or equal to about 10%.

In general, the reaction may be performed at any suitable temperature. For instance, the reacting step may be performed at a temperature of greater than or equal to about −20° C. and less than or equal to about 200° C. (e.g., greater than or equal to about 0° C. and less than or equal to about 200° C., greater than or equal to about −20° C. and less than or equal to about 150° C., greater than or equal to about 0° C. and less than or equal to about 100° C., greater than or equal to about 5° C. and less than or equal to about 75° C., greater than or equal to about 10° C. and less than or equal to about 50° C., greater than or equal to about 15° C. and less than or equal to about 30° C.). In some instances, the reacting step may be performed around room temperature (e.g., greater than or equal to about 15° C. and less than or equal to about 30° C.).

In some embodiments, the ratio of monomers of formula (IV) to total monomers of formula (V) and (VI) may be selected to achieve the desired weight percentage of the precursor of the pharmaceutically active agent. In certain embodiments, the ratio of monomers of formula (IV) to total monomers of formula (V) and (VI) is greater than or equal to about 0.5 to 1 and less than or equal to about 2 to 1 (e.g., greater than or equal to about 0.9 to 1 and less than or equal to about 2 to 1.) In some embodiments, the method further comprising reacting

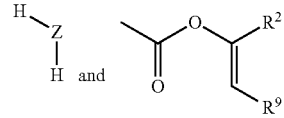

in the presence of [Ir(cod)Cl]$_2$ and Na$_2$CO$_3$ to form monomers of formula (IV), wherein Z, R$^2$, and R$^9$ are defined as described herein.

In some embodiments, the method may comprise reacting a polymer of formula (II) or (III) with monomer or another polymer to form a copolymer (e.g., block copolymer). For example, a block copolymer (e.g., diblock copolymer) comprising one or more ketal, monothioketal, and/or ketal bonds and a PEG block may be formed by reacting the R$^8$ of the polymer of Formula (III) with a terminal end of a PEG having the structure:

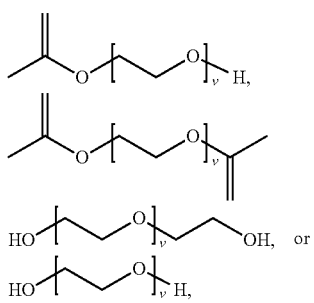

wherein v is 3-100,000 (e.g, 3-75,000; 3-50,000; 3-25,000; 3-10,000; 3-5,000; 3-1,000; 3-500; 3-100; 5-100,000; 5-75,000; 5-50,000; 5-25,000; 5-10,000; 5-5,000; 5-1,000; 5-500; 5-100; 10-100,000; 10-75,000; 10-50,000; 10-25,000; 10-10,000; 10-5,000; 10-1,000; 10-500; 10-100; 20-100,000; 20-75,000; 20-50,000; 20-25,000; 20-10,000; 20-5,000; 20-1,000; 20-500; or 20-100).

As another example, a copolymer (e.g., alternating copolymer) comprising one or more ketal, monothioketal, and/or ketal bonds and a polyethylene glycol may be formed when X and M are ethylene glycol. In some embodiments, a copolymer (e.g., block copolymer) may be formed using a PEG block and one or more of the following monomers of formulae (IV), (V), and/or (VI):

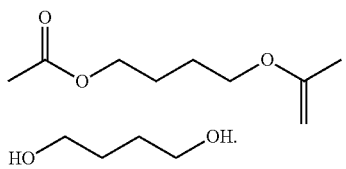

In some embodiments, a block copolymer (e.g., diblock copolymer) comprising one or more ketal, monothioketal, and/or ketal bonds and another polymer block (e.g., PEG block) may be formed by reacting the R$^8$ of the polymer of Formula (III) with a linker, such as the maleimide linker shown below, having suitable functional groups to react with the terminal end of the polymer of formula (III) and the other polymer.

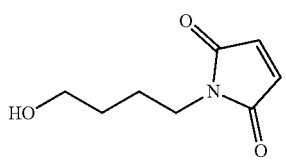 [SMILES: O=C1C=CC(=O)N1CCCCO]

For example, in embodiments in which the linker is the maleimide linker shown above, the hydroxyl group of the linker may react with the polymer of formula (III) and the maleimide may be react with the terminal end of another polymer to form a block copolymer.

Those of ordinary skill in the art will be aware of conditions and reagents for carrying out the synthetic methods described herein.

Non-limiting examples of suitable monomers of formula (IV) include:

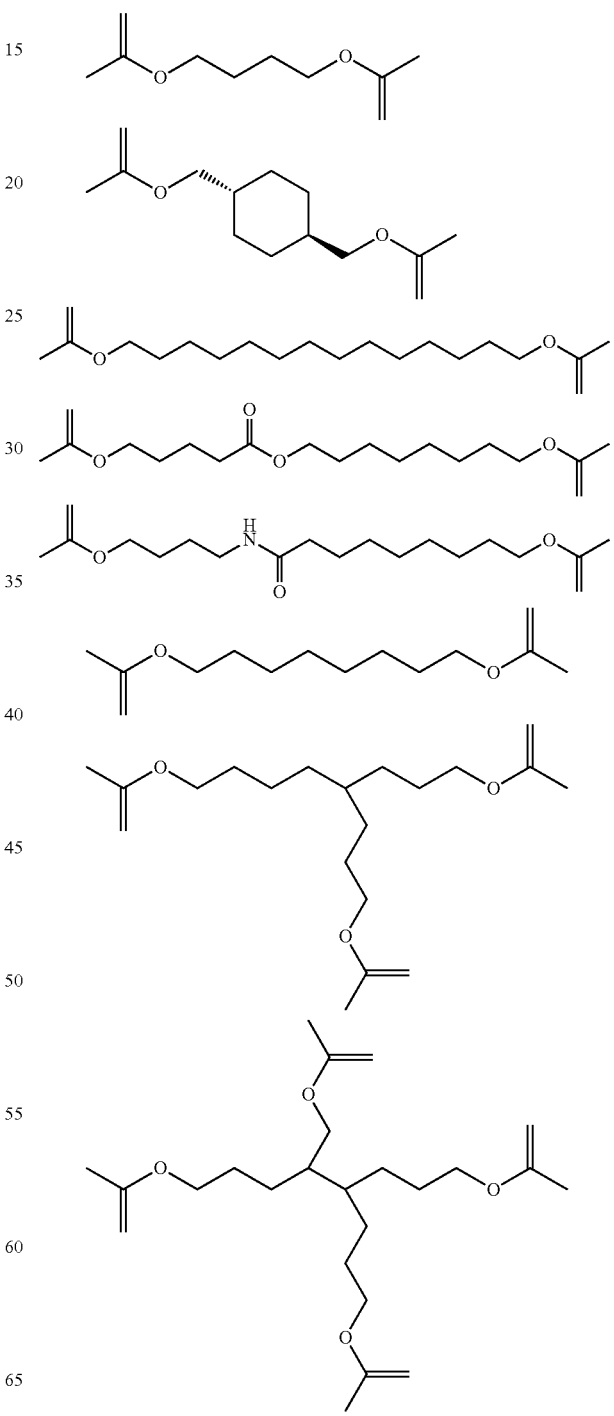

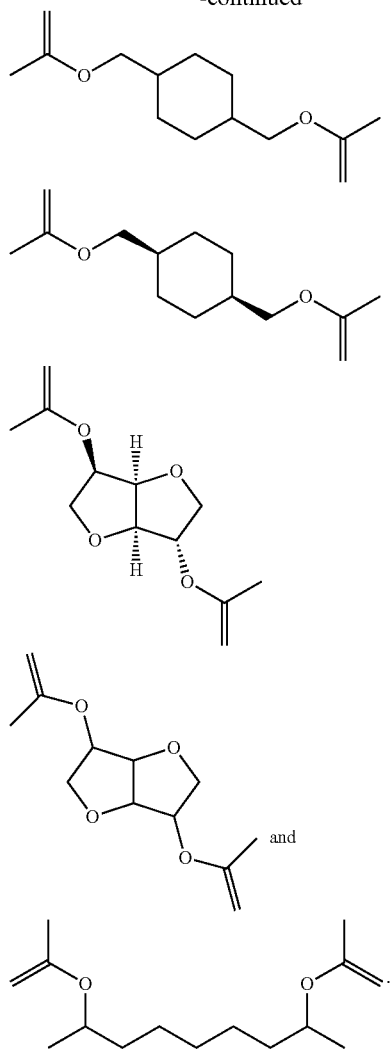
Non-limiting examples of suitable monomers of formula (V) include
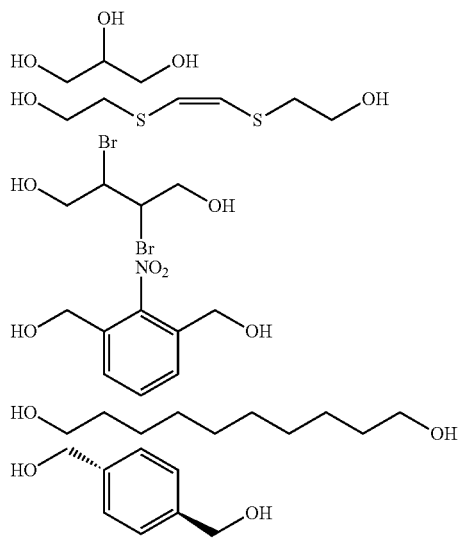
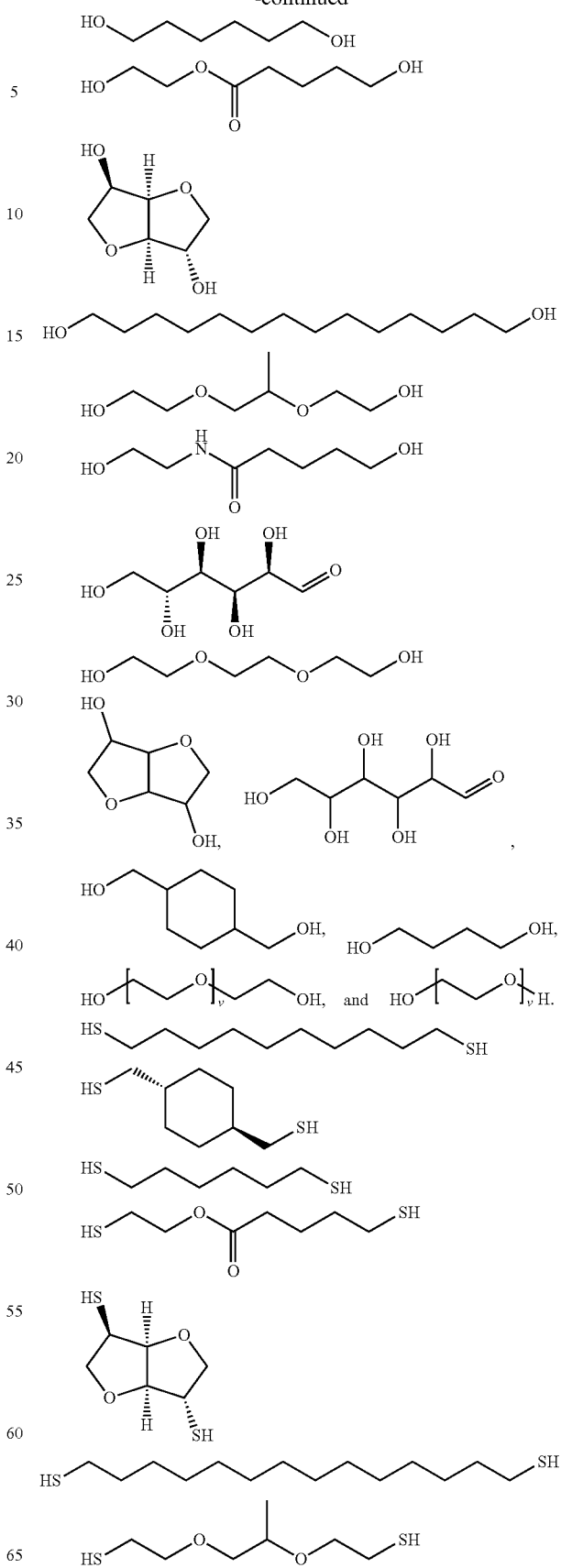

25
-continued
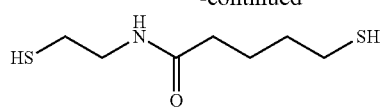
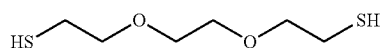
26
-continued
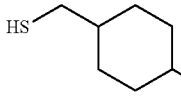 and 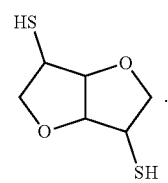.
Non-liming examples of pharmaceutically active agents that may be used directly or indirectly as monomer (V) include:
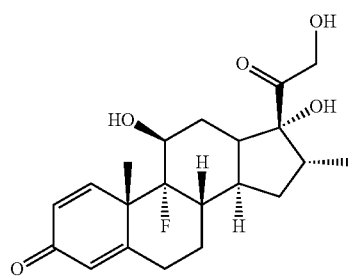
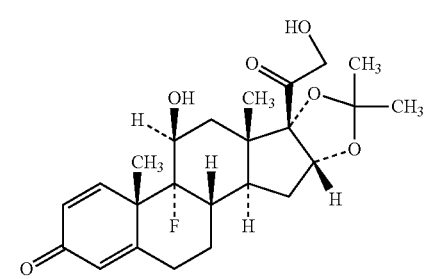
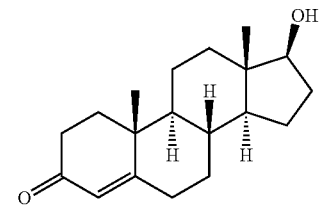
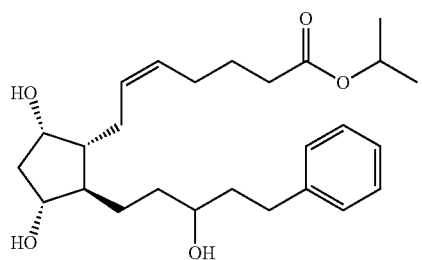
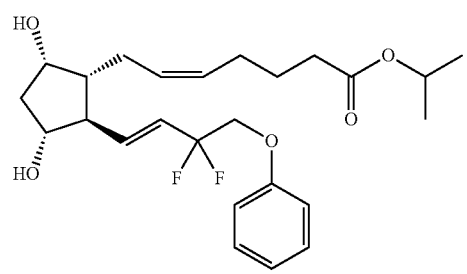
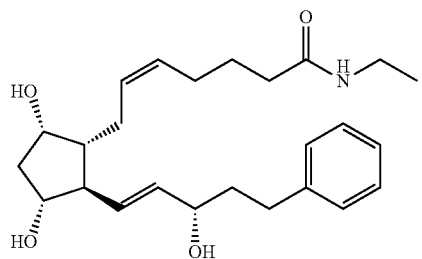
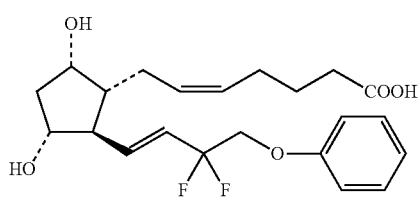
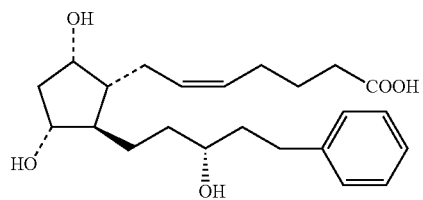
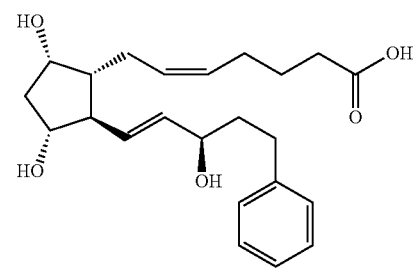
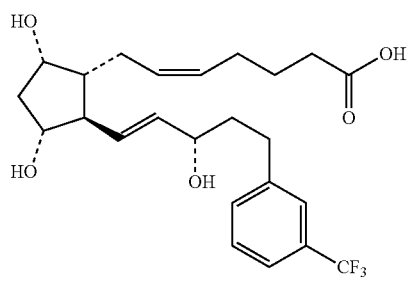
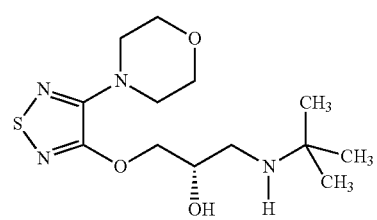

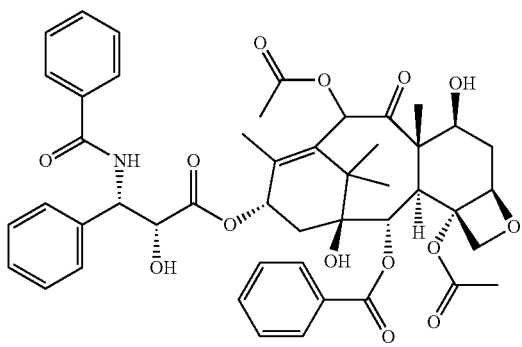
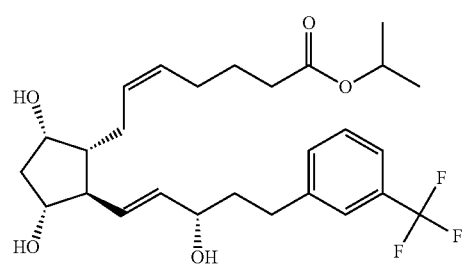
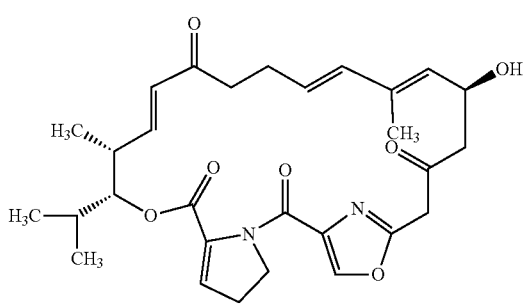
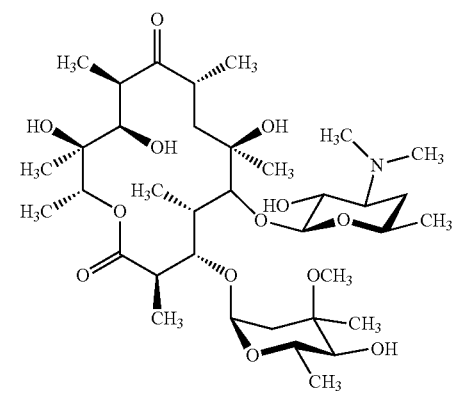
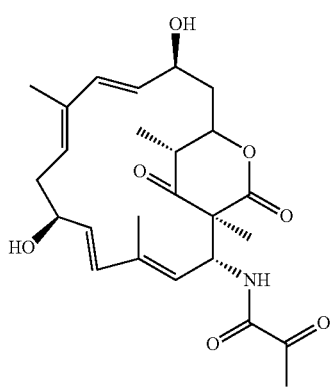
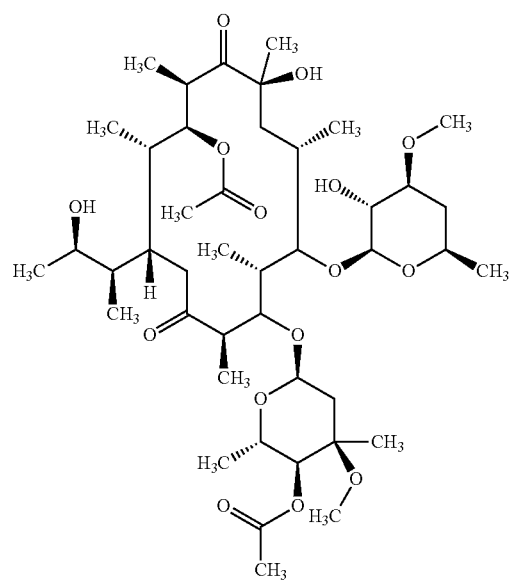
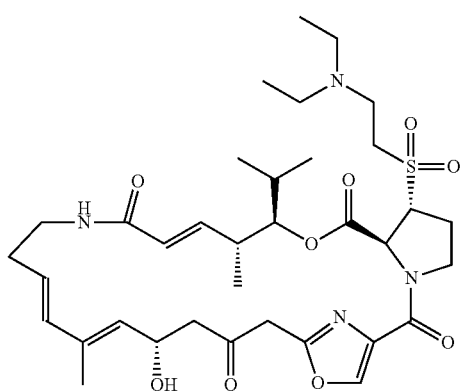
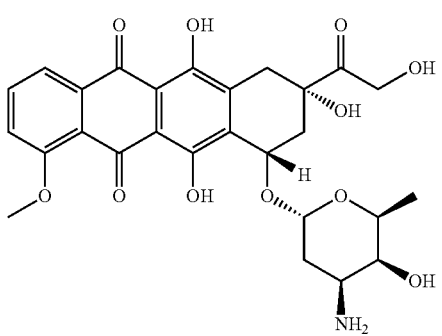

-continued
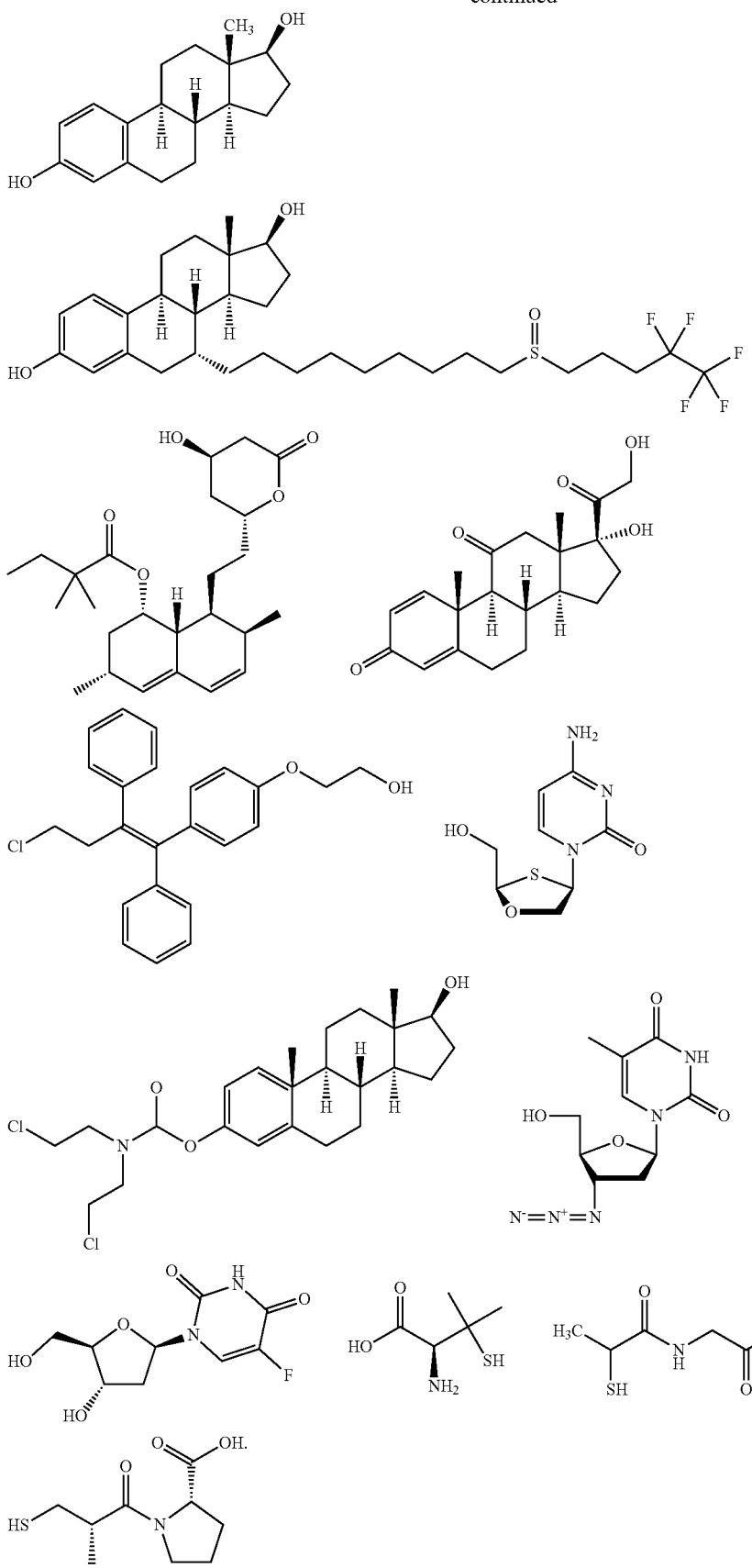

Compositions or polymers formed via the methods described herein may be particularly useful for administering an agent to a subject in need thereof. In some embodiments, the compositions are used to deliver a pharmaceutically active agent. The composition may be administered in any way known in the art of drug delivery, for example, orally, parenterally, intraocularly, intravenously, intramuscularly, subcutaneously, intradermally, transdermally, intrathecally, submucosally, sublingually, rectally, vaginally, etc. In some embodiments, the composition, formed as described herein, are particularly well-suited for the treatment of ophthalmic disorders (e.g., glaucoma).

Once the composition has been prepared, it may be combined with pharmaceutically acceptable excipients to form a pharmaceutical composition. As would be appreciated by one of skill in this art, the excipients may be chosen based on the route of administration as described below, the agent being delivered, and the time course of delivery of the agent. In some embodiments, the pharmaceutical composition comprising a therapeutically effective amount of the composition comprising a polymer comprising one or more repeat units of formula (I), a polymer comprising formula (II), or a polymer of formula (III); and one or more pharmaceutically acceptable excipients.

Pharmaceutical compositions of the present invention and for use in accordance with the present invention may include a pharmaceutically acceptable excipient. As used herein, the term "pharmaceutically acceptable excipient" means a nontoxic, inert solid, semi-solid or liquid filler, diluent, encapsulating material or formulation auxiliary of any type. Some examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen free water; isotonic saline; citric acid, acetate salts, Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., the particles), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, ethanol, U.S.P., and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacteria retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the inventive particles with suitable non irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the particles in a proper medium. Absorption enhancers can also be used to increase the flux of the compound across the skin. The rate can be controlled by either providing a rate controlling membrane or by dispersing the particles in a polymer matrix or gel.

The invention also provides kits for use in preparing or administering the inventive particles. A kit for forming particles may include the albumin and a dialdehyde as well as any solvents, solutions, buffer agents, acids, bases, salts, targeting agent, etc. needed in the particle formation process. Different kits may be available for different targeting agents. In certain embodiments, the kit includes materials or reagents for purifying, sizing, and/or characterizing the resulting particles. The kit may also include instructions on how to use the materials in the kit. The one or more agents (e.g., pharmaceutically active agent) to be encapsulated in the particle are typically provided by the user of the kit.

Kits are also provided for using or administering the inventive composition or pharmaceutical compositions thereof. The composition (e.g., particles) may be provided in convenient dosage units for administration to a subject. The kit may include multiple dosage units. For example, the kit may include 1-100 dosage units. In certain embodiments, the kit includes a week supply of dosage units, or a month supply of dosage units. In certain embodiments, the kit includes an even longer supply of dosage units. The kits may also include devices for administering the composition or a pharmaceutical composition thereof. Exemplary devices include syringes, spoons, measuring devices, etc. The kit may optionally include instructions for administering the inventive composition (e.g., particles) (e.g., prescribing information).

The term "monomer" as used herein, has its ordinary meaning in the art and may refer to a molecule or a moiety on a molecule that is capable of participating in a reaction to become a part of the essential structure of a polymer.

The term "pendant group" as used herein, refers to a group attached to the backbone of a polymer that is neither oligomeric nor polymeric.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_2$-s alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocycle" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Examples of $C_{5-6}$ carbocyclyl groups include cyclopentyl ($C_5$) and cyclohexyl ($C_5$). Examples of $C_{3-6}$ carbocyclyl groups include the aforementioned $C_{5-6}$ carbocyclyl groups as well as cyclopropyl ($C_3$) and cyclobutyl ($C_4$). Examples of $C_{3-8}$ carbocyclyl groups include the aforementioned $C_{3-6}$ carbocyclyl groups as well as cycloheptyl ($C_7$) and cyclooctyl ($C_8$). Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

As used herein, "heterocyclyl" or "heterocycle" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3-b]pyridinyl, 2,3-dihydrofuro[2,3-b] pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{1-4}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^d$d groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_1$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, -OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$, optionally substituted. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and claims. The invention is not intended to be limited in any manner by the above exemplary listing of substituents.

As used herein, the term "salt" refers to any and all salts, including pharmaceutically acceptable salt.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, use of the phrase "at least one" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

The term "particle" refers to a small object, fragment, or piece of a substance that may be a single element, organic material, or mixture thereof. Examples of particles include polymeric particles, coacervates, microparticles, nanoparticles, macroscopic particles, pellets, crystals, aggregates, composites, pulverized, and milled or otherwise disrupted matrices, each of which have an average characteristic dimension of about less than about 1 mm and at least 1 nm, where the characteristic dimension, or "critical dimension," of the particle is the largest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having an average characteristic dimension of less than about 1 micrometer and at least about 1 nanometer, where the characteristic dimension of the particle is the largest cross-sectional dimension of the particle.

The term "microparticle" refers to a particle having an average characteristic dimension of less than about 1 millimeter and at least about 1 micrometer, where the characteristic dimension of the particle is the largest cross-sectional dimension of the particle.

The terms "composition" and "formulation" are used interchangeably.

As used herein, the term "biocompatible" is intended to describe a material (e.g., particles, excipients) that is not toxic to cells. A material is "biocompatible" if its addition to cells in vitro results in less than 20% cell death, and their administration in vivo does not cause adverse effects.

As used herein, the term "biodegradable" is intended to describe a material that typically degrades over time when exposed to a biological system, e.g., through oxidation, hydrolysis, enzymatic attack, phagocytosis, or the like. For example, a biodegradable material can degrade over time when exposed to water (e.g., hydrolysis) or enzymes. In some cases, a biodegradable material is one that exhibits degradation (e.g., loss of mass and/or structure) when exposed to physiological conditions for at least about a month, at least about 6 months, or at least about a year. For example, the biodegradable material may exhibit a loss of mass of at least about 10%, at least about 20%, at least about 30%, at least about 40%, at least about 50%, at least about 60%, at least about 70%, at least about 80%, or at least about 90%. In certain cases, some or all of the degradation products may be resorbed or metabolized, e.g., into cells or tissues. For example, certain biodegradable materials, during degradation, release substances that can be metabolized by cells or tissues. For instance, polylactic acid releases water and lactic acid during degradation.

As used herein, the term "pharmaceutically active agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Pharmaceutically active agents include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/ Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. Preferably, though not necessarily, the pharmaceutically active agent is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the pharmaceutically active agent is a small molecule. Exemplary pharmaceutically active agents include, but are not limited to, anti-glaucoma agents, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, the term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions.

U.S. Provisional Patent Application Ser. No. 62/329,443, filed Apr. 29, 2016, entitled "Poly(Ketals) and Related Compositions and Methods," by Kohane, et al. is incorporated herein by reference in its entirety.

The following examples are intended to illustrate certain embodiments of the present invention, but do not exemplify the full scope of the invention.

Example 1

Development of biodegradable particulate drug delivery systems which can provide very prolonged drug release with a minimal initial burst and without undesirable degradation products is desirable for the treatment of chronic diseases. Polyketals are a new class of biomaterials, which are acid-responsive and biodegradable. In contrast to polyesters (e.g. PLGA), the degradation of polyketals yields pH-neutral products (ketone and alcohol). Biodegradable delivery systems able to release drugs in native form for extended periods (e.g. many months) are desirable, especially for treating chronic conditions. An approach to achieving that goal would be to incorporate drug molecules within the backbone of high molecular weight polyketals (drug-polyketal conjugate). Carriers made from such drug-polyketal conjugates could have enhanced drug loading, increased duration of release, and less initial burst release; these advances would be significant improvements over existing drug delivery systems. Facile methods of synthesizing relatively high molecular weight drug-polyketal conjugates have not yet been reported.

In this example, the synthesis of high molecular weight polyketals by reacting di-isopropenyl ether (DIPP) monomers with diol monomers, catalyzed by a Lewis acid through a simple addition polymerization, without producing side products is demonstrated, as shown in Scheme 1A.

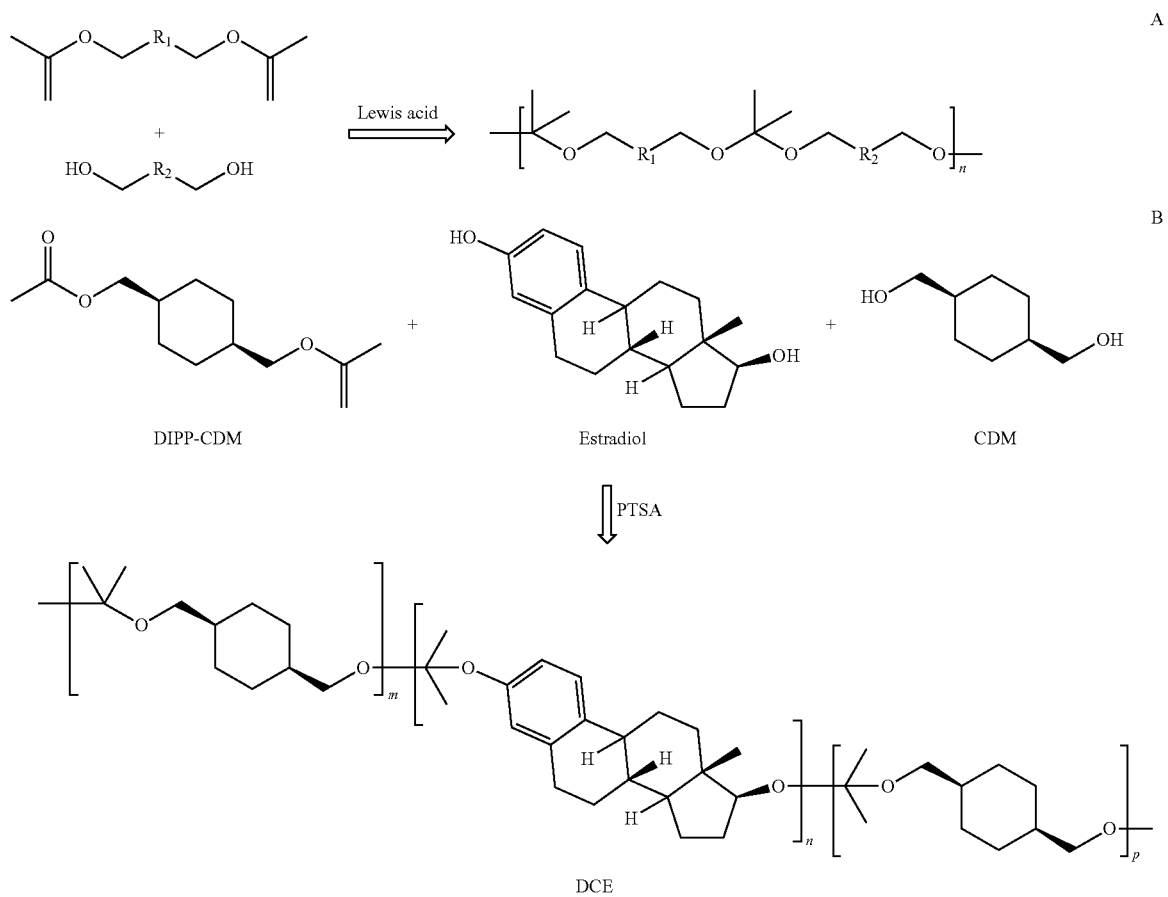

Scheme 1. Polyketal synthesis.

Scheme 1 shows (A) polyketal synthesis via Lewis acid catalyzed addition polymerization of di-isopropenyl ether monomers and diol monomers and (B) synthesis of estradiol-polyketal conjugate (DCE; m=n+p) via Lewis acid p-toluenesulfonic acid (PTSA) catalyzed addition polymerization of DIPP-CDM, estradiol and CDM.

Drugs containing two hydroxyl groups, such as estradiol, corticosteroids, and prostaglandins could be readily copolymerized with DIPP to form drug-polyketal conjugates. As proof-of-principle, a model drug (estradiol) was used to synthesize an estradiol-polyketal conjugate from which microparticles were made, as shown in Scheme B. Since estradiol was conjugated into the polymer via ketal bonds, their hydrolysis led to the release of estradiol from the estradiol-polyketal conjugate in its native form. The release kinetics from estradiol-polyketal conjugate microparticles, and from others composed of a blend of estradiol-polyketal conjugate and PLGA were studied. The hypothesis for the latter experiment was that the degradation of the acid-labile polyketal—and hence the release of estradiol in its native form—would be hastened by the local acidity produced by the concurrent degradation of PLGA.

Di-isopropenyl trans-1,4-cyclohexanedimethanol ether (DIPP-CDM) was synthesized from a primary diol (trans-1,4-cyclohexanedimethanol, CDM) and isopropenyl acetate through the addition-elimination sequence of alcohol and acetic acid using $[Ir(cod)Cl]_2/Na_2CO_3$ as a catalyst as shown in Scheme 2.

For step-growth polymerization of high molecular weight polymers, the purity of the monomers is crucial because impurities can interfere with polymerization. Equality of the molarities of the two different difunctional monomers is important, which can also be affected adversely by impurities. Initial attempts to purify DIPP-CDM using a silica gel column, which was acidic, did not yield DIPP-CDM due to the acid sensitivity of isopropenyl group. Addition of the organic base 0.1% triethylamine to the eluent solvent did not prevent the hydrolysis of DIPP-CDM. DIPP-CDM was stable in basic aluminum oxide columns but, due to the minor difference in polarity between DIPP-CDM and acetate side products (both are nonpolar), they could not be separated by this column. DIPP-CDM was successfully purified with a C18 preparative column. To prevent hydrolysis of DIPP-CDM in water/acetonitrile (eluent solvent), 0.1% triethylamine (organic base) was added, and DIPP-CDM was obtained as a white needle-like powder with a yield of 75 wt %. NMR spectra of DIPP-CDM in deuterated benzene $(C_6D_6)$ confirmed the structure of DIPP-CDM. The peak of the protons of the double bond of isopropenyl ether was observed at 3.88-3.93 ppm and the peaks of acetate protons from side products (monoacetate-CDM and diacetate-CDM) (2.12 ppm, shown in the $^1H$ NMR spectrum before purification) were not detected after purification. The purity of DIPP-CDM as determined by HPLC was over 99%.

Polymerization of DIPP-CDM and diol monomers was subsequently performed at room temperature for 3.0 hours,

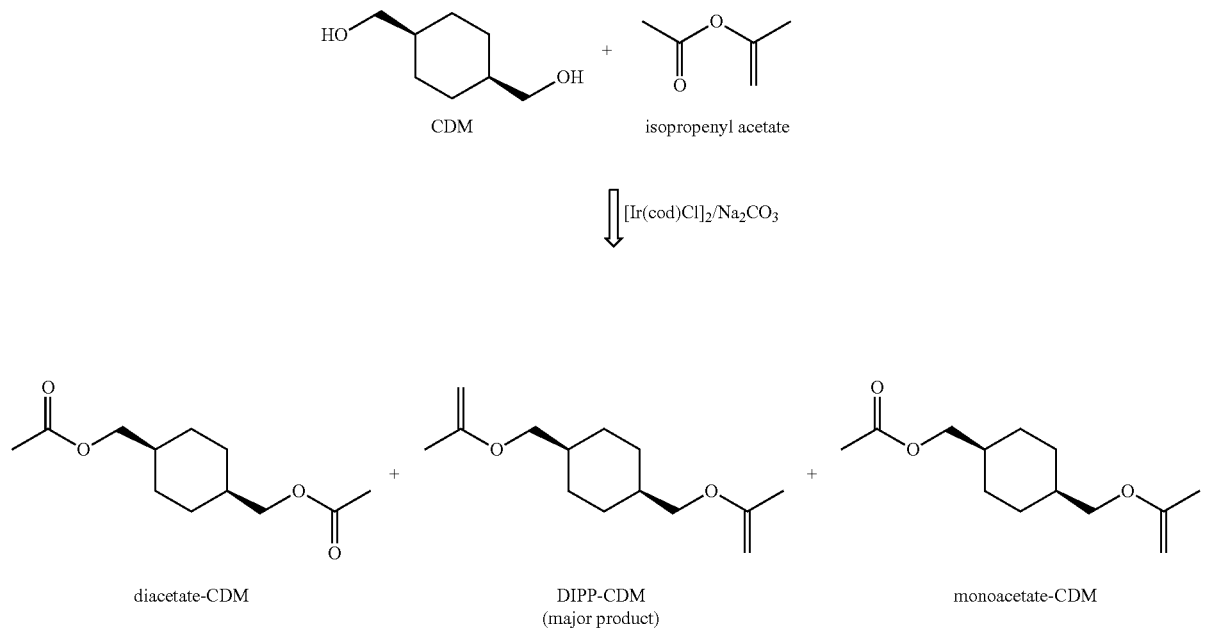

The progress of the reaction was monitored by NMR, which showed that transisopropenylation of isopropenyl acetate with CDM was the dominant reaction and produced a mixture of DIPP-CDM (major product) and minor side products (monoacetate-CDM and diacetate-CDM). The transacetate reaction produced monoacetate-CDM and diacetate-CDM, but this reaction was minor; only a small peak of acetate at 2.12 ppm was observed.

catalyzed by a Lewis acid: p-toluenesulfonic acid (PTSA, tetrahydrofuran as reaction solvent) or pyridinium p-toluenesulfonate (PPTS, chloroform as reaction solvent). Polyketals with varying compositions were synthesized from DIPP-CDM together with CDM, isosorbide (ISB), 1,4-butanediol and/or 1,10-decanediol (polyketals P1-P5 in Table 1).

TABLE 1

Synthesis and characterization of polyketals

| Polyketal[a] | Monomers (molar ratio)[b] | Reaction condition | $M_n$[c] | PDI[c] | Yield (wt %) |
|---|---|---|---|---|---|
| P1 | DIPP-CDM/CDM (1/1) | 0.5 mol % PPTS in CHCl$_3$ | N/A | N/A | 89 |
| P2 | DIPP-CDM/DCD (1/1) | 0.5 mol % PPTS in CHCl$_3$ | 193.1 | 1.7 | 78 |
| P3 | DIPP-CDM/CDM/DCD (2/1/1) | 0.5 mol % PPTS in CHCl$_3$ | 49.8 | 1.8 | 76 |
| P4 | DIPP-CDM/ISB (1/1) | 0.5 mol % PPTS in CHCl$_3$ | 45.3 | 1.9 | 75 |
| P5 | DIPP-CDM/BTD (1/1) | 0.5 mol % PPTS in CHCl$_3$ | 47.8 | 2.2 | 69 |
| DCE | DIPP-CDM/CDM/Estradiol (5/4/1) | 0.5 mol % PTSA in THF | 23.3 | 1.8 | 81 |
| DE | DIPP-CDM/Estradiol (1/1) | 0.5 mol % PTSA in THF | 6.5 | 1.6 | 25 |

[a]P1 to P5: polyketals without estradiol; DCE and DE: polyketal with estradiol.
[b]DIPP-CDM: di-isopropenyl trans-1,4-cyclohexanedimethanol ether, CDM: trans-1,4-cyclohexanedimethanol, DCD: 1,10-decanediol, BTD: 1,4-butanediol, ISB: isosorbide.
[c]determined by GPC.

The polymers were purified by precipitation into their anti-solvents to remove catalyst and unreacted monomers. High yields (69-89 wt %) and molecular weights in the range of 45-193 kDa) were obtained. Addition polymerization between DIPP monomers and diol monomers resulted in a significant increase of polyketal molecular weight compared to the results of a previously reported ketal exchange method ($M_n$<3 kDa). All the polyketals were water-insoluble and could presumably be used to prepare nanoparticles or microparticles for drug delivery.

Using the polymerization procedure above, estradiol, a diol drug widely used in hormonal therapy, was copolymerized (13.8 wt % of reagents) with CDM and DIPP-CDM in THF to produce an estradiol-polyketal conjugate (abbreviated DCE). Free estradiol was removed by repeated precipitation of DCE into methanol. $^1$H NMR spectra of DCE showed a peak at 7.15 ppm characteristic of estradiol. In addition, the proton shift of the methyl group of the ketal bond at 1.27 ppm suggested the successful polymerization of estradiol and DIPP-CDM. The $M_n$ of DCE determined by GPC was 23.3 kDa as shown in Table 1. The drug loading of DCE, determined by degradation by acid treatment in methanol, was 11.5 wt %, with a loading efficiency of 83.3 wt %. A maximum drug loading of 37.8% was achieved by copolymerizing DIPP-CDM with estradiol only (DE), with a loading efficiency of 69.0%. The lower loading efficiency was probably due to the steric hindrance around the hydroxyl group in estradiol. The $M_n$ of DE was 6.5 kDa, lower than that of DCE. DCE was used in subsequent studies.

DCE microparticles were prepared by the single emulsion method to be approximately 10 μm in diameter, as shown in Table 2, for easy injectability through a 27G needle and so that they would persist in tissue.

TABLE 2

Characterization of microparticles

| Microparticles | Size (μm)[a] | Drug loading (wt %)[b] | Yield (wt %) |
|---|---|---|---|
| DCE | 10.3 +/− 3.4 | 11.1 +/− 0.4 | 96.0 |
| DCE/PLGA | 13.7 +/− 4.3 | 6.0 +/− 0.1 | 67.2 |
| PLGA | 12.1 +/− 6.2 | 1.0 +/− 0.1 | 81.6 |

[a]determined by Coulter Counter;
[b]HPLC was used to measure the drug loading.

The yield of DCE microparticles was 96 wt % and their drug loading was 11.1 wt %. In contrast, the estradiol content in PLGA microparticles made by an analogous process (see Methods in Example 2) was 1.0 wt %, with an encapsulation efficiency of 49.6%.

The release of estradiol from DCE microparticles in mini dialysis devices in PBS (phosphate-buffered saline) was studied at pH 7.4 (physiological pH) and at pH 5.0 to document pH-lability. At predetermined time intervals, dialysis media were completely replaced, and the concentration of estradiol was determined by HPLC. HPLC and LC-MS analyses confirmed that estradiol was released from DCE microparticles in its native form at pH 7.4 as shown in FIGS. 2A-2D. Other degradation byproducts of DCE microparticles are likely to be acetone and CDM. No burst release was observed, and the time to release 50% of estradiol from DCE microparticles at pH 7.4 was ~14 weeks as shown in FIG. 1A. In comparison, at pH 7.4 PLGA microparticles exhibited burst release, released 50% of estradiol in less than one week, and all the estradiol was released in 4 weeks, before degradation of PLGA microparticles was complete. No oligomers of estradiol conjugates were detected by HPLC in the release media from DCE microparticles. In contrast, conjugates of drugs to polyester polymers (such as PLGA, PLA) release the native forms of drugs over a relatively short period (typically less than a month) and subsequently release soluble carboxyl group-containing oligomer-drug conjugates. At pH 5, DCE microparticles released 50% of their estradiol in 3 days, indicating that their degradation was acid-sensitive as shown in FIG. 1A. This pH-sensitivity may be useful in applications such as intracellular and anti-cancer drug delivery.

Figure 3A:
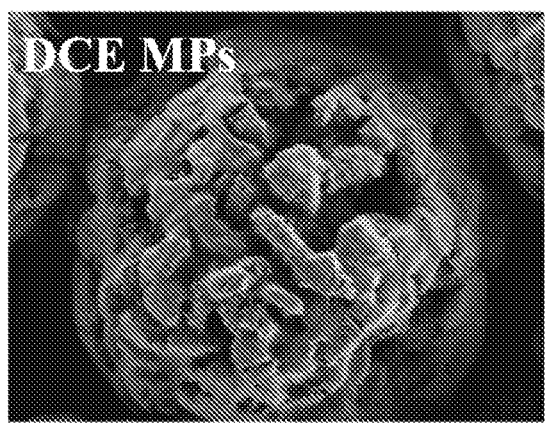
FIGS. 3A-3B show SEM images of DCE and DCE/PLGA microparticles prepared by the single emulsion method.
Figure 3B:
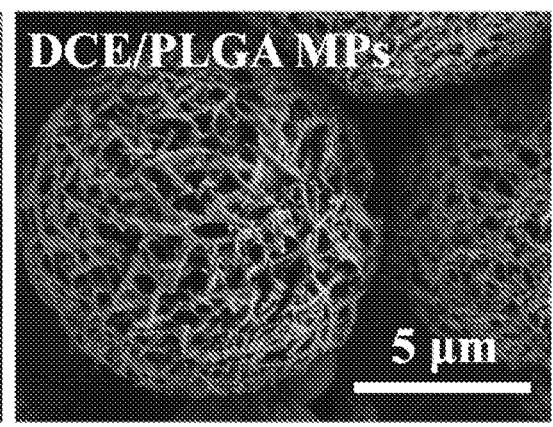

Given the acid-catalyzed degradation of polyketals, it was hypothesized that drug release from the polyketal particles could be modulated by co-incorporating PLGA, the degradation of which is known to create a local acidic microenvironment in microparticles. Microparticles with 50 wt % DCE and PLGA (50:50, ester terminated, $M_W$ 24,000-38,000) were prepared (abbreviated as DCE/PLGA microparticles; ~14 μm, Table 2) with a yield of 67.2 wt % and drug loading of 6.0 wt %. Scanning electron microscopy (SEM) showed that DCE microparticles and DCE/PLGA microparticles were spherical (see FIGS. 3A-3B). We documented that PLGA induced an acidic microenvironment in DCE/PLGA microparticles by producing maps of the ratio of the fluorescence intensity at 450 nm to that at 520 nm ($I_{450\ nm}/I_{520\ nm}$) of LysoSensor™ Yellow/Blue dextran, encapsulated within the particles; a higher $I_{450}/I_{520}$ indicates a higher pH. The pH in PLGA microparticles was lower than in DCE/PLGA microparticles, which was in turn lower than in DCE microparticles. This low-pH microenvironment was the likely cause of the much more rapid release of estradiol from DCE/PLGA, compared to DCE microparticles.

The biocompatibility of DCE microparticle was evaluated in the rat after injection at the sciatic nerve; this location is useful because there are nerve, muscle and connective tissues in close proximity. On dissection 4 and 21 days after injection, microparticles were visible at the injection site (see FIGS. 4A-4F). Tissues were sectioned and stained with hematoxylin and eosin by standard protocols. By light microscopy, in all tissues, a mass of particles was identified next to the muscle and/or nerve. On higher magnification, the mass was seen to contain particle-shaped lucencies (the remainder of particles dissolved in the staining process) and inflammatory cells. Macrophages, lymphocytes, and occasional neutrophils were observed on Day 4, while macrophages, lymphocytes and occasional foreign-body giant cells were observed on Day 21. The degrees of inflammation outside of the particle mass and of myotoxicity were scored (see Methods in SI). Scores were low at both time points, with minimal myotoxicity, and mild inflammation that improved from day 4 to 21 (p=0.04) but scores were low on Day 4 and Day 21, as shown in FIGS. 4A-4F and Table 3.

TABLE 3

Biocompatibility of DCE microparticles

| Scale | Score[a] Day 4 | Day 21 | U test (Day 4 vs Day 21)[b] |
|---|---|---|---|
| Inflammation (score 0-4) | 2.5 (1.5-3.0) | 1 (0.5-1) | p = 0.04 |
| Myotoxicity (score 0-6) | 0 (0-0.5) | 0 (0-0.5) | ns |

[a]Values are median score values (please see Methods) with interquartile ranges in parentheses (n = 4);
[b]Histological scores were compared for statistical significance using Mann-Whitney U-tests.

Deeper layers within the muscle had normal morphology without any signs of inflammation. The nerve tissue appeared intact. These results were similar to results obtained with polyester microparticles injected at the same location.

In summary, a facile and efficient method to synthesize di-isopropenyl ether monomer and high molecular weight polyketals by Lewis acid catalyzed addition polymerization of di-isopropenyl ether and diol monomers has been developed. Estradiol was used as a model drug in the synthesis of a hydrophobic estradiol polyketal conjugate. Because estradiol itself is a building block of the polymer, drug loading was high, and estradiol release was slow. In vitro release of native estradiol from estradiol-polyketal conjugate microparticles occurred over more than 4 months. Drug release kinetics was altered by adding PLGA. Tissue reaction in vivo was benign. These materials may be useful for very prolonged sustained delivery as well as for pH-responsive biomaterials.

Example 2

This example describes the procedures used in Example 1.

Materials: Anhydrous chloroform, anhydrous $Na_2CO_3$, bis(1,5-cyclooctadiene)diiridium(I) dichloride ($[Ir(cod)Cl]_2$), triethylamine (TEA), p-toluenesulfonic acid monohydrate (PTSA), pyridinium p-toluenesulfonate (PPTS) and Tween@ 80 were received from Sigma-Aldrich (Milwaukee, Wis., USA) and used directly Isopropenyl acetate (IPPA) and 1,4-butanediol (BTD) were ordered from Sigma-Aldrich (Milwaukee, Wis., USA) and distilled before use. Trans-1,4-cyclohexanedimethanol (CDM) was purchased from Tokyo Chemical Industry (TCI, Philadelphia, Pa., USA) and dried under vacuum before use. Anhydrous tetrahydrofuran (THF), anhydrous toluene and anhydrous pyridine were purchased from Sigma-Aldrich. 1,10-decanediol (DCD), 1,6-hexanediol (HXD) and estradiol were received from Sigma-Aldrich and dried under vacuum before use. PLGA (lactide:glycolide 50:50, ester terminated, $M_w$ 24,000-38,000) is purchased from Sigma-Aldrich. Lysosensor Yellow/Blue™ dextran, 10,000 Mw (pH-sensitive dye) was purchased from Thermo Fisher Scientific (Waltham, Mass., USA).

Synthesis of DIPP-CDM: Anhydrous $Na_2CO_3$ (8.54 g) was dried in a 250 ml flask for 1.5 h at 180° C. under vacuum. The flask was cooled and flushed with $N_2$. Then, CDM (5.76 g, 40 mmol) and $[Ir(cod)Cl]_2$ (0.97 g) were added. The mixture was dried using several nitrogen-vacuum purging cycles. Then, 24 mL IPPA and 40 mL toluene were added. The mixture was heated at 100° C. Six hours later, the mixture was cooled and diluted with ether, filtered, and dried under vacuum. The residue was extracted with hexane. Hexane was removed by rotary evaporation. DIPP-CDM (2.7 g) was recrystallized from ACN twice and dried under vacuum.

The synthesis was confirmed by high-performance liquid chromatography (HPLC) and nuclear magnetic resonance (NMR). It is notable that the acid sensitivity of DIPP-CDM prevents its detection when trifluoroacetic acid, a common HPLC additive, was present in the eluent. Signals of DIPP-CDM were also not observed when $CDCl_3$ was used as an NMR solvent, since $CDCl_3$ can react with light and oxygen to form phosgene and DCl. It is notable that DIPP was so acid sensitive that DIPP hydrolyzed completely in the silica column even in the presence of triethylamine. In addition, the polarity of DIPP and the transacetate side product during the reaction (such as mono-ester and di-ester substituted compounds) are so similar that they come off of a basic aluminum oxide column together rapidly, leading to the failure of purification.

DIPP-CDM was also purified by column chromatography (CombiFlash® Rf, 100 g HP C18, Teledyne Isco, Lincoln, Nebr., USA). To prevent the hydrolysis of monomer in $H_2O$/ACN, 0.1% TEA was added. C18 column chromatography yielded a higher quantity of polymerization grade monomer (6.8 g, 75 wt %) than did recrystallization (30 wt %).

The chemical shifts in the NMR spectra of DIPP-CDM were assigned as below ($C_6D_6$ as NMR solvent, Cambridge Isotope Laboratories, Inc., Tewksbury, Mass., USA): $^1$H NMR ($C_6D_6$, ppm, 400 MHz): δ 3.93-3.88 (d, J=9.0 Hz, 4H), 3.38-3.35 (d, J=6.65 Hz, 4H), 1.81 (s, 6H), 1.79-1.73 (d, J=6.65 Hz, 4H), 1.61-1.47 (m, 2H), 0.93-0.81 (m, 4H)$^3$C NMR ($C_6D6$, ppm, 400 MHz): δ 159.88, 80.93, 72.48, 37.51, 29.18, 20.77.

Polymerization: The following represents a typical preparation of a polyketal. Under anhydrous conditions, 224 mg (1 mmol) of DIPP-CDM and 106 mg (1 mmol) of 1, 6-hexanediol were weighed into a 10 mL flask, and the mixture was dissolved in 3 mL of anhydrous chloroform (containing amylene as a stabilizer). Then 0.2 mL of PPTS (5 mol) in anhydrous chloroform (containing amylene as a stabilizer) was added. After 3.0 h, the solution was stopped by the addition of several drops of TEA and the mixture was added into methanol dropwise to precipitate the polymers. The polymers were stored in a desiccator under high vacuum until dry.

The following represents a typical preparation for an estradiol-polyketal conjugate. Under anhydrous conditions, 224 mg (1 mmol) of DIPP-CDM, 115.2 mg (0.8 mmol) of CDM and 54.4 mg estradiol (0.2 mmol) were weighed into a 10 mL flask, and the mixture was dissolved in 2 mL of anhydrous THF. Then 0.2 mL of PTSA (5 µmol) in anhydrous THF was added. After 3.0 h, the solution was stopped by the addition of several drops of TEA and the mixture was added into methanol dropwise to precipitate the polymer. The polymers were stored in a desiccator under high vacuum until dry.

Polymer Characterization: The composition of polymers was determined by $^1$H NMR (Varian 400 MHz equipped with 5 mm AutoX OneProbe and Varian 7600 autosampler) (Varian, Inc., Palo Alto, Calif., USA). Molecular weights were determined by gel permeation chromatography (GPC) using tetrahydrofuran as the solvent and polystyrene as standards. GPC was performed using a Waters system equipped with a 2400 differential refractometer, 515 pump, and 717-plus autosampler (Waters Corporation, Milford, Mass., USA). The flow rate was 1 mL/min. The Styragel columns (Waters) and detector were maintained at 35° C.

Microparticle preparation: Microparticles were prepared by a single o/w emulsion method. One hundred mg of polymer solution in 1.26 mL chloroform was homogenized at 8000 rpm for 1 min (Silverson L5M-A homogenizer, Silverson Machines, Inc., Chesham Bucks, UK) into a 50 mL solution of 0.5% polyvinyl alcohol PBS solution. The emulsion was then added into 100 mL 0.05 wt % PVA PBS solution and stirred for 6 h at room temperature to evaporate chloroform. Microparticles were collected by centrifugation at 2000 rpm for 6 min and washed twice by distilled water. Microparticles were then lyophilized to dryness and stored at −20° C. Estradiol loaded PLGA microparticles were prepared as described.

Microparticle characterization: Lyophilized microparticles were fixed onto carbon support film Cu grids (CF200F1-Cu, Electron Microscopy Sciences, Hatfield, Pa., USA) and further attached to specimen stubs using double-coated tape. The specimens were imaged with JEOL Model 6320 FV field emission scanning electron microscope (Massachusetts Institute of Technology Department of Materials Science and Engineering Electron Microscopy Center, JEOL Ltd., Tokyo, Japan) using 2.5-5 kV accelerating voltage at 10 mm working distance. The particle size and distribution of microparticles were determined by light microscopy (FSX100, Olympus Corporation, Tokyo, Japan) with a calibrated eyepiece and with a Coulter Multisizer (Coulter Electronics Inc., Luton, UK).

To determine the loading of estradiol in estradiol-polyketal conjugate and microparticles, the polymer or microparticles were suspended in methanol and hydrolyzed by addition of two drops of 1M HCl to release estradiol at 37° C. overnight. The concentration of estradiol was then determined by HPLC (Agilent 1260 Infinity, Agilent Co., Palo Alto, Calif., USA) equipped with reverse phase C18 column (Poroshell 120 EC-C18, 4.6×100 mm, i.d. 2.7 μm, Phenomenex, Torrance, Calif., USA) at room temperature and a flow rate of 1.0 mL/min using an aqueous solution of acetonitrile/water (40/60) as the mobile phase. Estradiol was detected by UV absorbance at λ=281 nm.

The loading and loading efficiency of estradiol in conjugate were calculated with these formulae:

$$\text{loading of estradiol in conjugate} = \frac{\text{actual measured mass of estradiol}}{\text{mass of polymer}}$$

$$\text{loading efficiency of estradiol in conjugate} = \frac{\text{actual measured loading of estradiol in conjugate}}{\text{theoretical (feed) loading of estradiol in conjugate}}$$

The loading of estradiol in microparticles was calculated according to formula as below:

$$\text{loading of estradiol in microparticles} = \frac{\text{actual measured mass of estradiol}}{\text{mass of microparticles}}$$

To measure the actual loading of estradiol in microparticles, they were suspended in methanol and hydrolyzed by addition of two drop of 1M HCl to release estradiol at 37° C. overnight. The amount of estradiol in microparticles was then analyzed by HPLC (Agilent 1260 Infinity, Agilent Co.). Chromatography was performed using an Agilent 1260 Infinity HPLC system with reverse phase C18 column (Poroshell 120 EC-C18, 4.6×100 mm, i.d. 2.7 μm, Phenomenex, Torrance, Calif., USA) at room temperature and a flow rate of 1.0 mL/min using an aqueous solution of acetonitrile/water (40/60) as the mobile phase. Estradiol was detected by UV absorbance at k=281 nm.

In vitro release: Microparticles were suspended in 0.5 mL phosphate-buffered saline (PBS, pH 7.4) and incubated in mini dialysis devices (Slide-A-Lyzer™ MINI Dialysis Device, 20K MWCO, 0.5 mL, Thermo Fisher Scientific Inc, Rockford, Ill., USA) outside of which was 14 mL PBS buffer containing 0.1 wt % Tween 80 (pH=7.4 and 5.0) at 37° C. (n=4). At predetermined intervals, the release medium was completely replaced with fresh media containing 0.1 wt % Tween 80. The concentration of drug was then analyzed by HPLC (Agilent 1260 Infinity, Agilent Co.). Chromatography was performed using an Agilent 1260 Infinity HPLC system with reverse phase C18 column at room temperature and a flow rate of 1.0 mL/min. An aqueous solution of acetonitrile/water (40/60) was used as the mobile phase. Estradiol was detected by UV absorbance at λ=281 nm.

The cumulative drug release percent (Er) was calculated by the following equation:

$$Er(\%) = \frac{V_e \sum_{1}^{n-1} C_i + V_0 C_n}{m_{estradiol}} \times 100\%$$

where $m_{estradiol}$ represents the amount of estradiol in the microparticles, $V_0$ is the whole volume of the release media ($V_0$=14.5 mL), $V_e$ is the volume of the replace media ($V_e$=14 mL), and $C_n$ represents the concentration of estradiol in the nth sample. Four groups of replicate measurements were carried out for each time point.

Preparation of microparticles encapsulating pH-sensitive probes: All the microparticles containing the pH-sensitive dye were prepared by a w/o/w double emulsion-solvent evaporation method. In brief, 100 μl of the dye solution in pure water (0.05-5.0 mg/mL) was added into 1.0 mL of the polymer solution in chloroform (40 mg/mL). Then, the mixture was sonicated using a VC505 Vibra-cell sonicator (Sonics & Materials, Inc., Newtown, Conn., USA) equipped with microtip probe at 120 J for 1 min to prepare a w/o emulsion. The resulting w/o emulsion was immediately added to 10.0 mL of PVA solution in PBS (2.5 wt %), and this mixture was homogenized using a Silverson L5M-A homogenizer at 3,000 rpm for 1 min to prepare a w/o/w emulsion. The w/o/w emulsion was poured slowly into 100 mL of PVA solution in PBS (1.0 wt %) and stirred at room temperature for 5-6 hours to remove chloroform. The hardened microparticles were collected by centrifugation (3,000 rpm×5 min), washed by pure water twice, and lyophilized.

Mapping of the pH microenvironment inside microparticles: Mapping of ratio of fluorescence intensity at 450 nm to that at 520 nm ($I_{450\,nm}/I_{520\,nm}$) inside the microparticles was conducted in order to investigate the microenvironment pH. The pH-sensitive dye used in this study changes its $I_{450\,nm}/I_{520\,nm}$ value according to the pH value (e.g., lower $I_{450\,nm}/I_{520\,nm}$ corresponds to lower pH, and higher $I_{450\,nm}/I_{520\,nm}$ corresponds to higher pH).

The microparticles (4.0 mg) were incubated in 1.0 mL of PBS (pH 7.4) at 37° C. for 1 day. Then, the suspension was centrifuged, the supernatant was removed, and fresh PBS was added to suspend the microparticles. The imaged with a Carl Zeiss LSM 710 (Carl Zeiss MicroImaging, Inc., Thornwood, N.Y., USA) confocal laser scanning microscope (CLSM) equipped with a coherent pulse laser and a C-Apochromat 63X water immersion objective lens. The fluorescent dye was excited by two-photon excitation at 728 nm, and the emissions at 450 nm and 520 nm were recorded. All the parameters, including laser power, detection gain and scan speed, were fixed throughout all the CLSM measurements. The acquired CLSM images were processed using Image J software (available at http://rsb.info.nih.gov/ij/) as previously described. In brief, the CLSM images were processed by frame averaging (N=8), neighborhood averaging, and then a median filter. Subsequently, the threshold for accepted values was 2<pixel value<245. Finally, the $I_{450\,nm}/I_{520\,nm}$ values for each pixel were calculated. In order to do quantitative comparisons, average $I_{450}\,nm/I_{520\,nm}$ values inside of each microparticle was also calculated. When calculating these values, microparticles with 'black holes', which correspond to the area where the fluorescence values were saturated, were not selected in order to avoid any artificial effects on the results.

In vivo biocompatibility study: Perineural injections were performed with a 20-gauge needle under isoflurane/oxygen anesthesia as described. In brief, each rat was injected with 8 mg of DCE microparticles suspended in 0.2 mL PBS after gentle shaking (<5 s) in preparation for injection. On Days 4 and Day 21, rats were euthanized with carbon dioxide. The sciatic nerve and surrounding muscle were harvested and fixed in 10% formalin (10% Formalin Fixative, Neutral, Phosphate Buffered, EK Industries Inc., Joliet, Ill., USA). Muscle specimens were processed to produce hematoxylin and eosin-stained slides. The samples were scored for inflammation (0-4) and myotoxicity (0-6). The inflammation score was a subjective assessment of severity. The myotoxicity was as follows: 0=normal; 1=perifascicular internalization; 2=deep internalization (>5 cell layers), 3=perifascicular regeneration, 4=deep regeneration, 5=hemifascicular regeneration, 6=holofascicular regeneration.

Statistical analyses: Data relating to the characterization of particles were reported as means with standard deviations. Statistical analysis was conducted by one-way analysis of variance (ANOVA) followed by a Tukey posthoc test using KaleidaGraph (Synagy Software, Reading, Pa.). In all cases, a p-value<0.05 was considered to reflect statistical significance.

Because of their non-normal distributions, histological scores were reported as medians with interquartile ranges, and analyzed for significance using Mann-Whitney U-tests using GraphPad Prism 6.0 (Graphad Software, La Jolla, Calif., USA). p-value<0.05 was considered to reflect statistical significance.

Example 3

This is a prophetic example of the formation of estradiol-poly(monothiolketal).

Typically, the drug-poly(monothiol ketal-ketal) conjugate was synthesized by copolymerization of diol, dithiol, drug (diol or more hydroxyl groups bearing molecules) and di-isopropenyl ether monomer (such as di-isopropenyl trans-1,4-cyclohexanedimethanol ether, DIPP-CDM) in solvent using Lewis acid as catalyst.

The following represents a typical preparation for an estradiol-poly(monothiol ketal-ketal) conjugate. Under anhydrous conditions, 224 mg (1 mmol) of DIPP-CDM, 60.1 mg (0.4 mmol) of 1,6-hexanedithiol, 57.6 mg (0.4 mmol) of CDM and 54.4 mg estradiol (0.2 mmol) were weighed into a 10 mL flask, and the mixture was dissolved in 2 mL of anhydrous THF. Then 0.2 mL of PTSA (5 μmol) in anhydrous THF was added. After 3.0 h, the solution was stopped by the addition of several drops of TEA and the mixture was added into methanol dropwise to precipitate the polymer. The polymers were stored in a desiccator under high vacuum until dry.

The reaction conditions for making polymers can vary based on the monomers used. For examples, the reaction solvent can be toluene, chloroform, tetrahydrofuran, dichloromethane, acetone acetonitrile, benzene, or their mixture and so on; the reaction temperature can be in the range of −20° C. to 200° C.; the catalyst can be Lewis acid, such as p-toluenesulfonic acid monohydrate (PTSA) and pyridinium p-toluenesulfonate (PPTS); the amount of Lewis acid can be 0.001% to 10% by mole of monomers; methanol, water, hexane, cyclohexane, diethyl ether can be used to precipitate polymer.

Example 4

This example describes the formation of a Tafluprost-polyketal conjugate.

Typically, the tafluprost-polyketal conjugate (TPKC) was synthesized by copolymerization of tafluprost and/or diol with di-isopropenyl ether monomer (such as di-isopropenyl trans-1,4-cyclohexanedimethanol ether, DIPP-CDM) in a solvent using Lewis acid as catalyst as shown in Scheme 3.

Scheme 3. Synthesis of tafluprost-polyketal conjugate

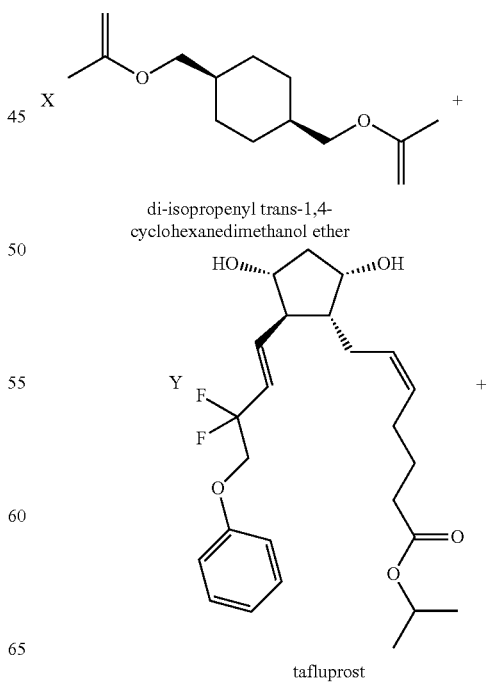

di-isopropenyl trans-1,4-cyclohexanedimethanol ether tafluprost

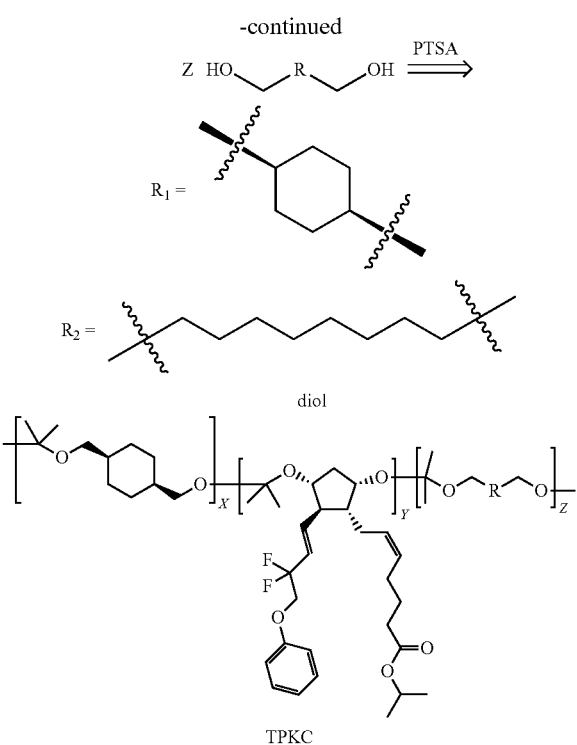

Scheme 3 shows the synthesis of tafluprost-polyketal conjugate via addition polymerization of di-isopropenyl trans-1,4-cyclohexanedimethanol ether, tafluprost and diols ($R_1$: trans-1,4-cyclohexanedimethanol, $R_2$: 1,10-decanediol).

The following represents a typical preparation. 224 mg (1 mmol) of DIPP-CDM, 115.2 mg (0.8 mmol) of CDM and 90.4 mg (0.2 mmol) of tafluprost were weighed into 10 mL flask, and the mixture was dissolved in 3 mL of anhydrous tetrahydrofuran. Then 0.2 mL of PTSA in anhydrous chloroform (1.90 mg PTSA, chloroform contains amylenes as stabilizer) was added. After the exothermic reaction subsided, the solution was stopped by the addition of several drops of triethylamine and added into methanol dropwise to precipitate polymer. The polymers were put in desiccator under high vacuum until dryness. The polymers were purified by precipitation into their anti-solvents to remove catalyst and unreacted monomers. High yields of about 80 wt % and molecular weights in the range of 5-40 kDa were obtained. All the polyketals were water-insoluble and could presumably be used to prepare nanoparticles or microparticles for drug delivery.

Figure 5:
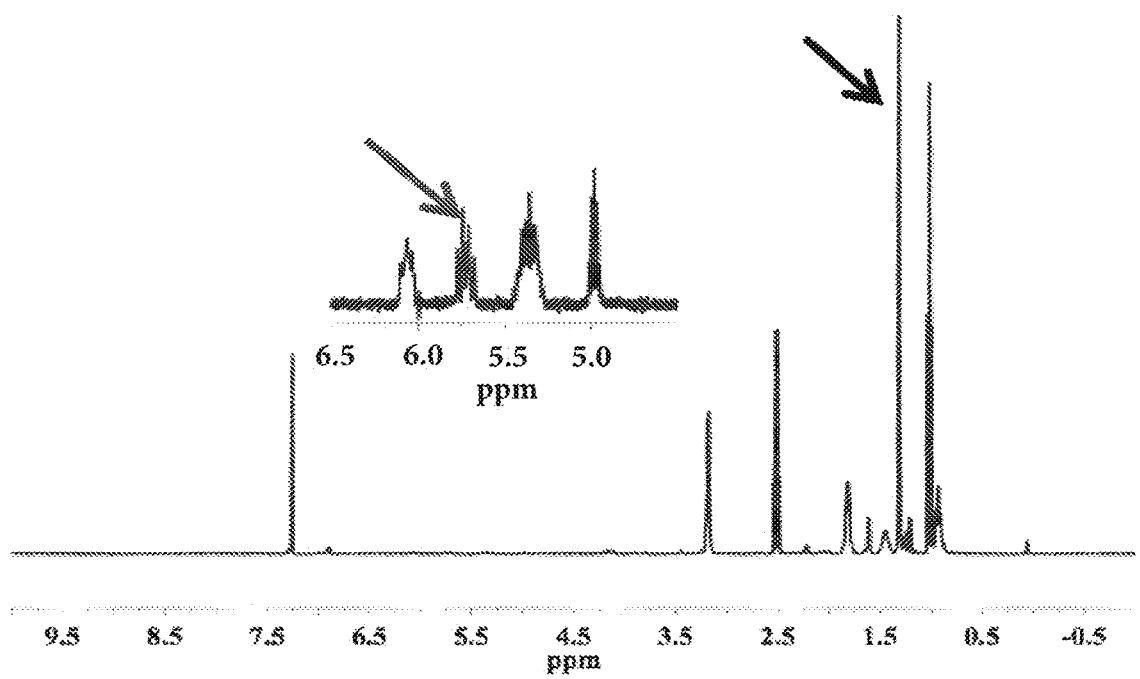
FIG. 5 shows a $^1H$ NMR spectra of a polymer including one or more repeat units containing one or more ketal bonds and a precursor of Tafluprost. The arrow shows the characteristic peak at 1.27 ppm of the ketal group. The inset is the magnified figure of peaks at 4.5-6.5 ppm and the arrow shows the characteristic peak of the Tafluprost precursor at 5.75 ppm, according to certain embodiments.

FIG. 5 shows a $^1H$ NMR spectra of the tafluprost-polyketal conjugate. The peak at 1.27 ppm of the ketal group indicated the successful of polymerization, while the characteristic proton peak of tafluprost at 5.75 ppm confirmed the successful incorporation of tafluprost in polyketals. The drug loading of tafluprost-polyketal conjugate, determined by degradation by acid treatment in methanol, was 17 wt %, with a loading efficiency of 81 wt %.

Figure 6:
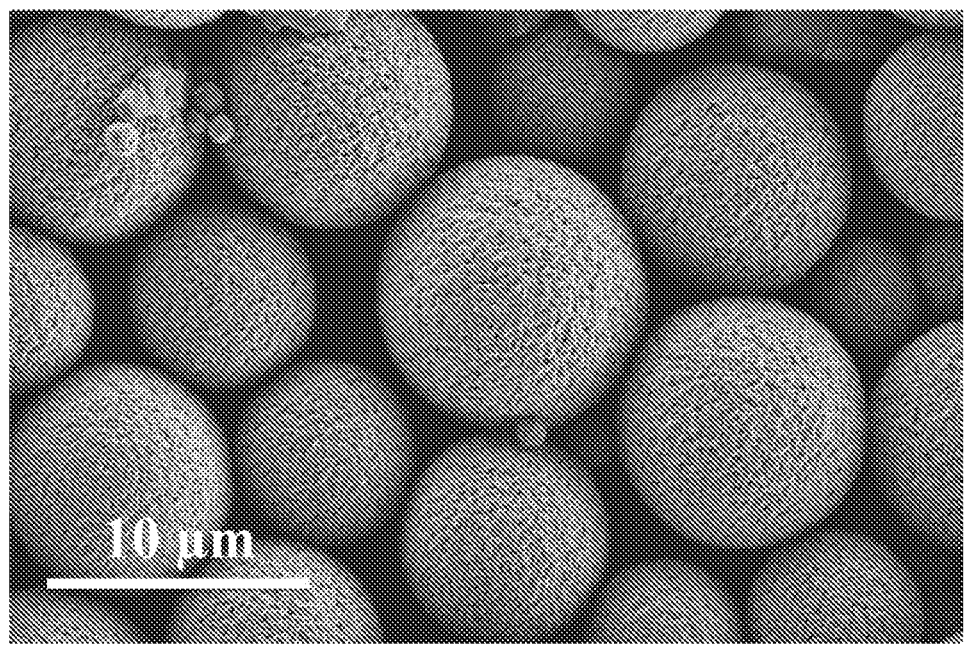
FIG. 6 shows a SEM image of microparticles formed from polymer including repeat units containing a ketal bond and a precursor of Tafluprost, according to certain embodiments.

Tafluprost-polyketal conjugate microparticles were prepared by the single emulsion method. The particles had a diameter of about 10 micrometers. Scanning electron microscopy (SEM) showed particles formed from the tafluprost-polyketal conjugate were spherical as shown in FIG. 6. The yield of tafluprost-polyketal conjugate microparticles was 85 wt % and their drug loading was 17 wt %.

Figure 7A:
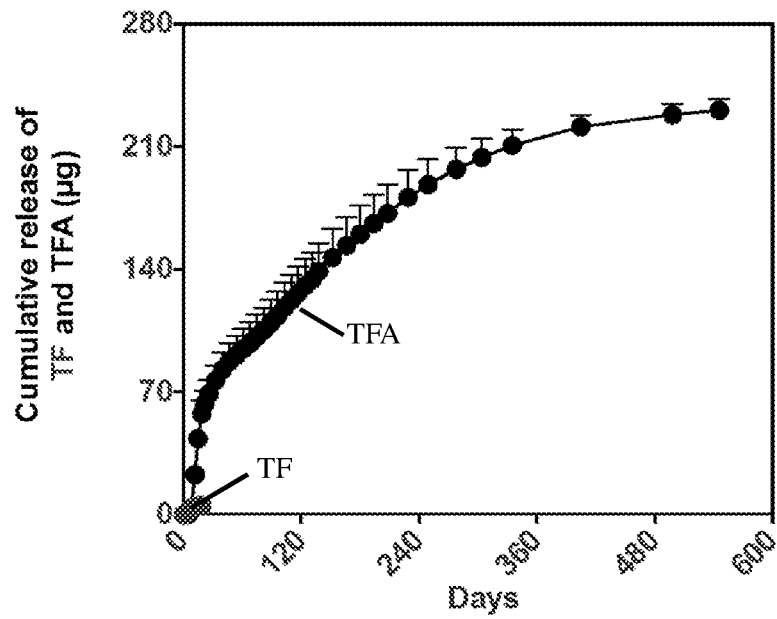
FIG. 7A shows a graph of the cumulative release of Tafluprost (TF) and Tafluprost acid (TFA) from microparticles, which were formed from polymer including repeat units containing a ketal bond and a precursor of Tafluprost acid, in PBS having a pH of 7.4. The data are means+/−SD; n=4.
Figure 7B:
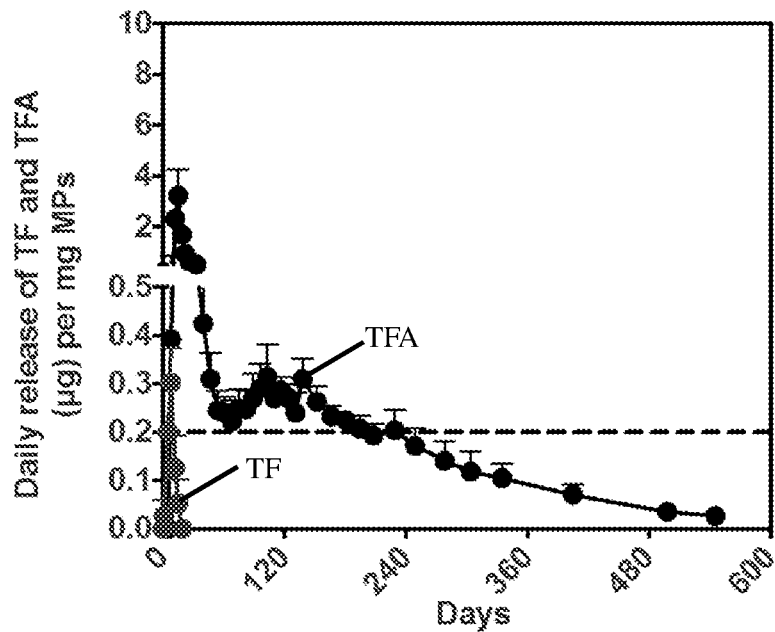
FIG. 7B shows a graph of the daily release of Tafluprost (1) and Tafluprost acid (2) from microparticles, which were formed from polymer including repeat units containing a ketal bond and a precursor of Tafluprost acid, in PBS having a pH of 7.4. The data are means+/−SD; n=4.

The release of tafluprost and tafluprost acid from the microparticles in mini dialysis devices in PBS (phosphate-buffered saline) was studied at pH 7.4 (physiological pH). At predetermined time intervals, dialysis media were completely replaced, and the concentration of tafluprost and tafluprost acid was determined by HPLC. As shown in FIGS. 7A-7B, no burst release was observed. The daily release of tafluprost and tafluprost acid was shown in FIG. 7B.

The biocompatibility of tafluprost-polyketal conjugate microparticles was evaluated in the rat after subconjunctival injection. On dissection 4 and 14 days after injection, ophthalmic tissues were sectioned and stained with hematoxylin and eosin by standard protocols. By light microscopy, in all tissues, no myotoxicity was observed. On day 4, acute inflammation was observed, while on day 14, mild chronic inflammation was observed, as shown in FIGS. 8A-8B.

Example 5

This is a prophetic example of the formation of tafluprost-poly(monothiol ketal) conjugate.

Typically, the drug-poly(monothiol ketal-ketal) conjugate was synthesized by copolymerization of diol, dithiol, drug (diol or more hydroxyl groups bearing molecules) and di-isopropenyl ether monomer (such as di-isopropenyl trans-1,4-cyclohexanedimethanol ether, DIPP-CDM) in solvent using Lewis acid as catalyst.

The following represents a typical preparation for an tafluprost-poly(monothiol ketal-ketal) conjugate. Under anhydrous conditions, 224 mg (mmol) of DIPP-CDM, 60.1 mg (0.4 mmol) of 1,6-hexanedithiol, 57.6 mg (0.4 mmol) of CDM and 90.5 mg tafluprost (0.2 mmol) were weighed into a 10 mL flask, and the mixture was dissolved in 2 mL of anhydrous THF. Then 0.2 mL of PTSA (5 μmol) in anhydrous THF was added. After 3.0 h, the solution was stopped by the addition of several drops of TEA and the mixture was added into methanol dropwise to precipitate the polymer. The polymers were stored in a desiccator under high vacuum until dry.

The reaction conditions for making polymers can vary as described in Example 3.

Example 6

This example describes the formation of a Latanoprost-polyketal conjugate.

Scheme 4. Synthesis of latanoprost-polyketal conjugate

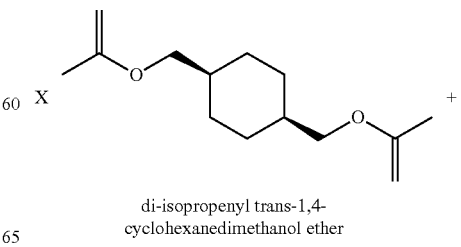

di-isopropenyl trans-1,4-cyclohexanedimethanol ether

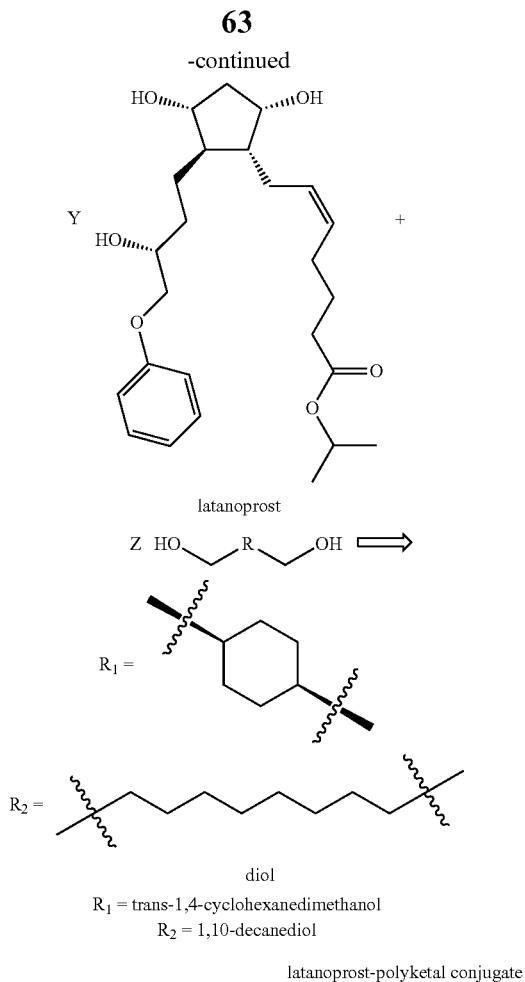

latanoprost-polyketal conjugate

Scheme 4 shows the synthesis of latanoprost-polyketal conjugate via addition polymerization of di-isopropenyl trans-1,4-cyclohexanedimethanol ether, tafluprost and diols ($R_1$: trans-1,4-cyclohexanedimethanol, $R_2$: 1,10-decanediol). X:Y:Z=5:1:4. LPKC-1: R=$R_1$; LPKC-2: R=0.4*$R_1$+ 0.6*$R_2$.

Typically, LPKC was synthesized by copolymerization of latanoprost and/or diol with di-isopropenyl ether monomer (such as di-isopropenyl trans-1,4-cyclohexanedimethanol ether, DIPP-CDM) in a solvent using Lewis acid as catalyst (Scheme 2).

The following represents a typical preparation. 224 mg (1 mmol) of DIPP-CDM, 115.2 mg (0.8 mmol) of CDM and 85.6 mg (0.2 mmol) of latanoprost were weighed into 10 mL flask, and the mixture was dissolved in 3 mL of anhydrous tetrahydrofuran. Then 0.2 mL of PTSA in anhydrous chloroform (1.90 mg PTSA, chloroform contains amylenes as stabilizer) was added. After the exothermic reaction subsided, the solution was stopped by the addition of several drops of triethylamine and added into methanol dropwise to precipitate polymer. The polymers were put in desiccator under high vacuum until dryness.

The reaction conditions for making polymers can vary as described. The peak at 1.27 ppm of the ketal group indicated the successful of polymerization, while the characteristic proton peak of tafluprost at 4.9 ppm confirmed the successful incorporation of latanoprost in polyketals.

Example 7

This is a prophetic example of the formation of latanoprost-poly(monothiol ketal) conjugate.

Typically, the drug-poly(monothiol ketal-ketal) conjugate was synthesized by copolymerization of diol, dithiol, drug (diol or more hydroxyl groups bearing molecules) and di-isopropenyl ether monomer (such as di-isopropenyl trans-1,4-cyclohexanedimethanol ether, DIPP-CDM) in solvent using Lewis acid as catalyst.

The following represents a typical preparation for an tafluprost-poly(monothiol ketal-ketal) conjugate. Under anhydrous conditions, 224 mg (1 mmol) of DIPP-CDM, 60.1 mg (0.4 mmol) of 1,6-hexanedithiol, 57.6 mg (0.4 mmol) of CDM and 86.5 mg latanoprost (0.2 mmol) were weighed into a 10 mL flask, and the mixture was dissolved in 2 mL of anhydrous THF. Then 0.2 mL of PTSA (5 μmol) in anhydrous THF was added. After 3.0 h, the solution was stopped by the addition of several drops of TEA and the mixture was added into methanol dropwise to precipitate the polymer. The polymers were stored in a desiccator under high vacuum until dry.

The reaction conditions for making polymers can vary as described.

Example 8

This is a prophetic example. Glaucoma is a chronic disease often associated with elevated intraocular pressure (IOP) and is the second leading cause of blindness in the world. Medicines against glaucoma in eye drops are rapidly removed by blinking, baseline and reflex lacrimation, and nasolacrimal drainage, so that only a very small fraction of drug penetrates into eye. Patient non-compliance with medication regimens is also a major problem. There is a need for a formulation which can be applied with minimal invasiveness and will reliably provide glaucoma medication to the eye for an extended period. That formulation should maintain the drug concentration in the therapeutic window for the intended duration of treatment following the single administration. The duration of effect should be tunable in the range of weeks to a year to reduce the frequency of treatment. The formulation should also have a high drug loading, be easy to manufacture, use and store, elicit a benign tissue reaction, and be completely biodegradable.

The key feature of this example is a method to synthesize hydrophobic, biodegradable ketal polymers composed of diol drugs and the naturally-occurring sugar isosorbide (ISB). In this example, the diol drug was the glaucoma medication tafluprost. Because the drug itself is a building block of the polymer, drug loading will be very high, and drug release will be governed directly by polymer degradation (vs. mere diffusion), making constant release easier to achieve. The polymer will degrade to pH-neutral compounds, i.e., ISB and tafluprost, which may minimize inflammation. Unlike most polymeric drug delivery systems, there will be no residual polymer after drug release is complete, facilitating repeated injections. This approach would constitute a major advance in the chronic treatment of glaucoma.

Tafluprost (Taflotan) is a potent anti-glaucoma prostaglandin analogue, which can lower IOP by increasing the outflow of aqueous humor from the anterior chamber of the eye. It is designed as an isopropyl ester prodrug of the active acid form, to enhance the penetration of drug through the cornea. Inside the eye, tafluprost is hydrolyzed by esterases to the biologically active acid. Although tafluprost is hydrophobic and can be encapsulated into poly(lactic-co-glycolic acid) (PLGA) MPs, drug loading is low and there is significant burst release. Moreover, polymer residue is present in tissue long after the drug is completely released, which can complicate repeated injection. This ketal polymeric MP formulation circumvents these issues, since the drugs are utilized as building blocks of the polymers: this will allow high drug loading, control release kinetics, and ensure that there is no polymer residue once drug is depleted.

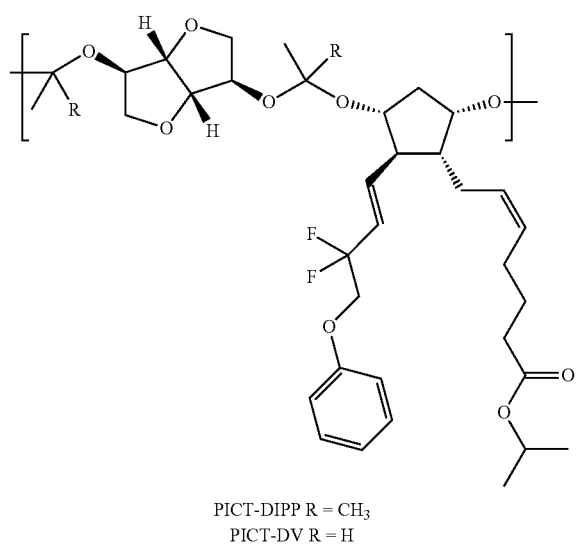

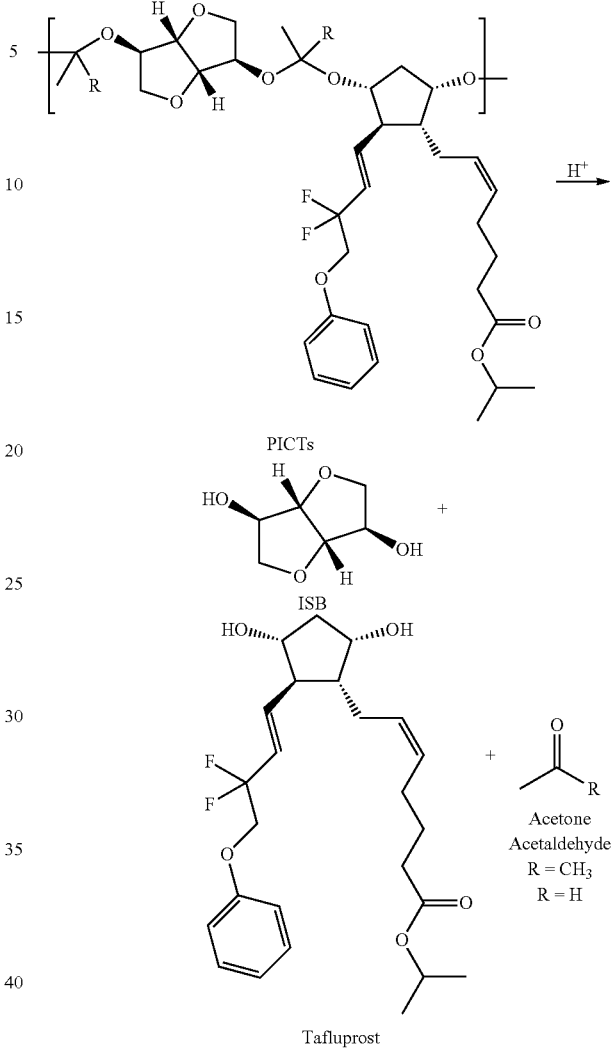

Scheme 5 shows (a) synthesis; (b) degradation mechanism. ISB: isosorbide, DIPP-ISB: di-isopropenyl-ISB, DV-ISB: di-vinyl-ISB, PICT-DIPP: poly(DIPP-ISB-co-tafluprost), PICT-DV: poly(DV-ISB-co-tafluprost).

To synthesize a polymer based on tafluprost (a poly(ISB-co-tafluprost), or PICT), ISB was functionalized with di-isopropenyl (DIPP) groups to obtain di-isopropenyl-ISB (DIPP-ISB), and then reacted DIPP-ISB with the diol tafluprost to achieve a high molecular weight ketal polymer (poly(DIPP-ISB-co-tafluprost); PICT-DIPP) via condensation polymerization. ISB is a non-toxic and biodegradable sugar which is used in medicine, e.g. in the treatment of closed-angle glaucoma.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A composition, comprising a polymer comprising one or more repeat units of formula (I):

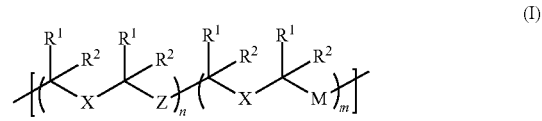

or a salt thereof, wherein:
each $R^1$ and $R^2$ is independently alkyl, optionally substituted;
each Z is independently a precursor of a pharmaceutically active agent;
each X is independently $-L^1-(R^3)_q-L^1-$, wherein each $R^3$ is optionally substituted with 0-5 $T^1$;
each M is independently $-L^2-(R^4)_r-L^2-$, wherein each $R^4$ is optionally substituted with 0-5 $T^2$;
each $R^3$ and $R^4$ is independently alkylene, heteroalkylene, carbocyclylene, heterocyclylene, alkenylene, heteroalkenylene, alkynylene, heteroalkynylene, arylene, or heteroarylene;
each $L^1$ and $L^2$ is independently —O— or —S—, wherein at least one of $L^1$ or $L^2$ is —S—;
each $T^1$ and $T^2$ is independently $R^5$ or —$R^6$—$Z^2$
each $R^5$ is alkyl, heteroalkyl, alkenyl, heteroalkenyl, heterocyclyl, hydroxyl, halo, thio, oxo, thioxo, amino, —$NO_2$, or acyl, optionally substituted;
each $R^6$ is alkylene, heteroalkylene, alkenylene, heteroalkenylene, —O—, —S—, —N(R)—, or acylene, optionally substituted;
$Z^2$ is a pendant precursor of a pharmaceutically active agent;
R is independently hydrogen or alkyl;
n is 1-5;
m is 0-5; and
q and r are independently 1-5;
provided that:
(i) the pharmaceutically active agent comprises two or more hydroxyl groups;
(ii) the pharmaceutically active agent is a steroid, prostaglandin, prostaglandin analog, or a prostamide;
(iii) the pharmaceutically active agent is an anti-glaucoma agent;
(iv) at least one of X, Z, or M comprises —S—; or
(v) m is greater than or equal to 1.

2. The composition of claim 1, wherein the steroid is selected from the group consisting of estradiol, dexamethasone, prednisone, testosterone, cholic acid, triamcinolone acetonide, triamcinolone, lanosterol, cortisol, and nandrolone.

3. The composition of claim 1, comprising particles comprising the polymer, wherein the largest cross-sectional dimension of the particles is less than or equal to about 1000 microns.

4. The composition of claim 1, wherein Z has the structure:

$$-T-Z^1-T-,$$

wherein:
Z is a portion of the pharmaceutically active agent;
T is $-L^3-$ or $-L^3-(R^7)_t-$;
$L^3$ is —O— or —S—;
$R^7$ is alkylene, heteroalkylene, alkenylene, heteroalkenylene, —O—, —S—, —N(R)—, or acylene, optionally substituted; and
each t is independently 0-5.

5. The composition of claim 1, wherein:
each $R^1$ and $R^2$ is independently $C_{1-2}$ alkyl;
each X is independently $-L^1-(R^3)_q-L^1-$, wherein each $R^3$ is optionally substituted with 0-3 $T^1$;
each M is independently $-L^2-(R^4)_r-L^2-$, wherein each $R^4$ is optionally substituted with 0-3 $T^2$;
each $R^3$ and $R^4$ is independently alkylene, heteroalkylene, carbocyclylene, heterocyclylene, heteroalkenylene, arylene, or heteroarylene;
R is independently hydrogen;
n is 1 or 2 and m is 0-2; and
q and r are independently 1-3.

6. The composition of claim 1, wherein at least one of $L^1$ or $L^2$ is —O—.

7. A pharmaceutical composition comprising:
a therapeutically effective amount of the composition of claim 1; and
one or more pharmaceutically acceptable excipients.

8. A method of treating an ophthalmic disorder in a patient, comprising:
administering the pharmaceutical composition of claim 7 to the patient.

9. A kit comprising:
a pharmaceutical composition as in claim 7; and
instructions for use of the composition in a subject.

10. An in vitro method of administering a composition to a cell, comprising:
administering the composition of claim 1 to a cell.

11. The composition of claim 1, wherein each Z is independently a precursor of an anti-glaucoma agent.

12. The composition of claim 11, wherein the anti-glaucoma agent is selected from the group consisting of prostaglandin analogs, beta blockers, alpha agonists, and carbonic anhydrase inhibitors.

13. The composition of claim 11, wherein the anti-glaucoma agent is selected from the group consisting of tafluprost, bimatoprost, travopost, latanoprost, timolol, unoprostone, tafluprost acid, latanoprost acid, and bimatoprost acid.

14. The composition of claim 11, wherein the anti-glaucoma agent is tafluprost.

* * * * *